(12) United States Patent
Liu et al.

(10) Patent No.: US 10,772,929 B2
(45) Date of Patent: Sep. 15, 2020

(54) USE OF PEPTIDE COMPOUNDS IN TREATING ACUTE PANCREATITIS

(71) Applicant: SHENZHEN HIGHTIDE BIOPHARMACEUTICAL, LTD., Shenzhen (CN)

(72) Inventors: Liping Liu, Manassas, VA (US); Ru Bai, Shenzhen (CN)

(73) Assignee: SHENZHEN HIGHTIDE BIOPHARMACEUTICAL, LTD., Shenzhen (CN)

( * ) Notice: Subject to any disclaimer, the term of this patent is extended or adjusted under 35 U.S.C. 154(b) by 0 days.

(21) Appl. No.: 16/094,881

(22) PCT Filed: May 11, 2017

(86) PCT No.: PCT/CN2017/084013
§ 371 (c)(1),
(2) Date: Dec. 4, 2018

(87) PCT Pub. No.: WO2018/205233
PCT Pub. Date: Nov. 15, 2018

(65) Prior Publication Data
US 2019/0216883 A1  Jul. 18, 2019

(51) Int. Cl.
*A61K 38/10* (2006.01)
*A61P 1/18* (2006.01)
*C07K 7/08* (2006.01)
*C07K 7/02* (2006.01)
*C07K 14/47* (2006.01)

(52) U.S. Cl.
CPC ............... *A61K 38/10* (2013.01); *A61P 1/18* (2018.01); *C07K 14/4733* (2013.01)

(58) Field of Classification Search
CPC .. A61K 38/10; A61P 1/18; C07K 7/08; C07K 7/02; C07K 14/4733; C07K 14/4738
USPC .............. 514/21.4, 21.5; 530/326, 327
See application file for complete search history.

(56) References Cited

U.S. PATENT DOCUMENTS

| | | | |
|---|---|---|---|
| 9,388,215 B2 * | 7/2016 | Liu | C07K 7/02 |
| 9,738,695 B2 * | 8/2017 | Liu | C07K 7/02 |
| 2015/0203538 A1 * | 7/2015 | Liu | C07K 7/02 514/21.4 |
| 2017/0002049 A1 * | 1/2017 | Liu | C07K 7/02 |
| 2018/0009861 A1 * | 1/2018 | Liu | C07K 7/02 |

OTHER PUBLICATIONS

Acute Pancreatitis from Merck Manual, pp. 1-8. Accessed Jan. 10, 2020.*

* cited by examiner

*Primary Examiner* — Julie Ha
(74) *Attorney, Agent, or Firm* — Milstein Zhang & Wu LLC

(57) ABSTRACT

Method of use of peptides and their analogs in the treatment of acute pancreatitis are described. The disclosed peptides and analogs can significantly lower the elevated blood amylase and lipase levels caused by acute pancreatitis, reduce the degree of injury observed in pancreatic histopathology caused by pancreatitis, and significantly lower the mortality rate of acute pancreatitis.

6 Claims, 7 Drawing Sheets

Specification includes a Sequence Listing.

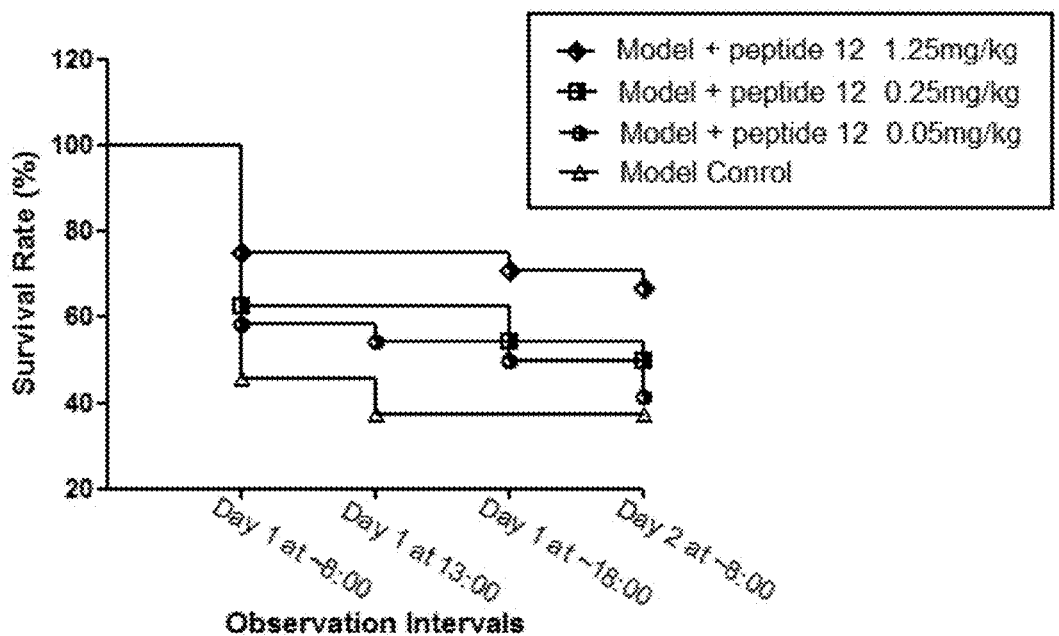
Figure 1. Beneficial effects of peptide No. 12 on the survival outcome in sodium taurocholate induced pancreatitis model
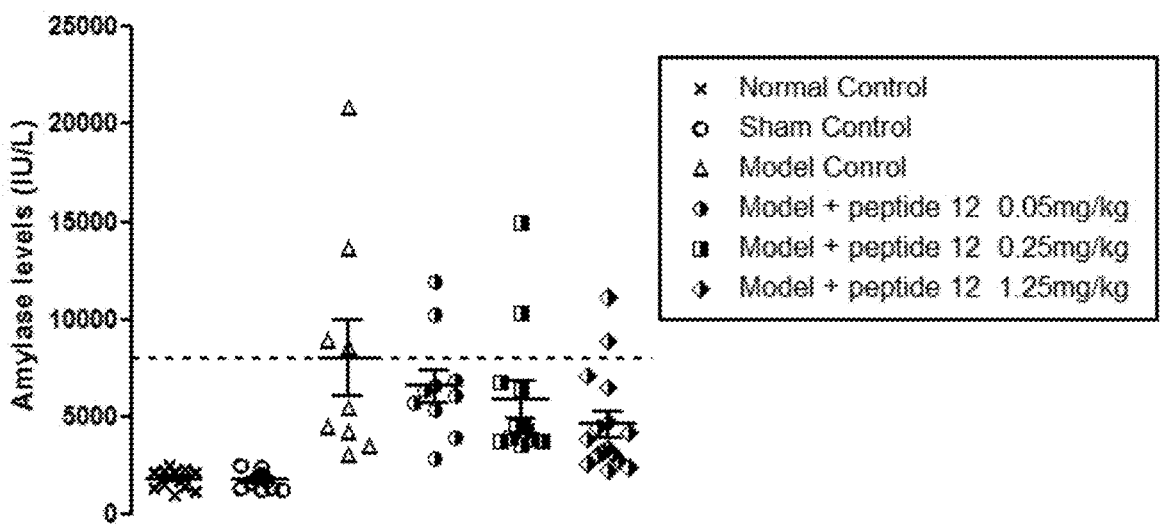
Figure 2. Beneficial effects of peptide No. 12 on the serum amylase levels in sodium taurocholate induced pancreatitis model

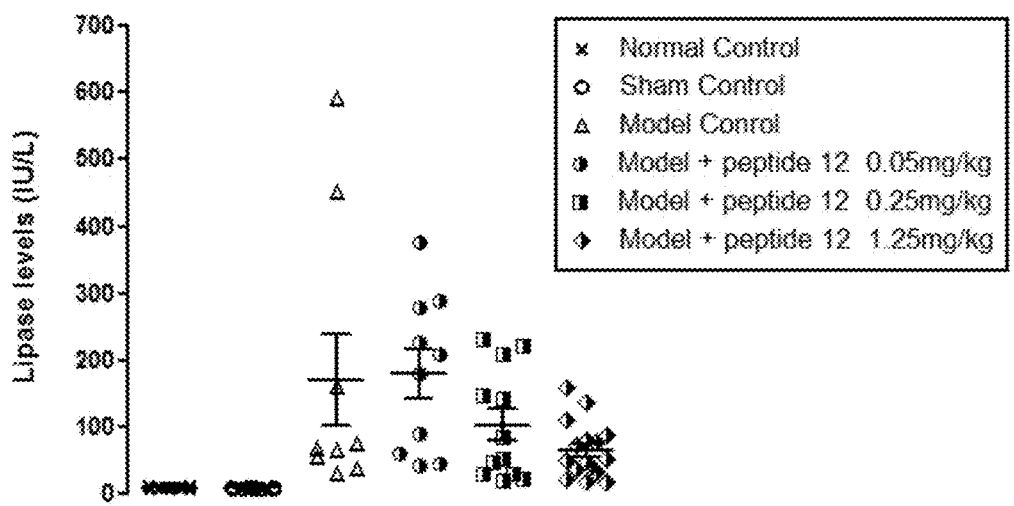
Figure 3. Beneficial effects of peptide No. 12 on the serum lipase levels in sodium taurocholate induced pancreatitis model
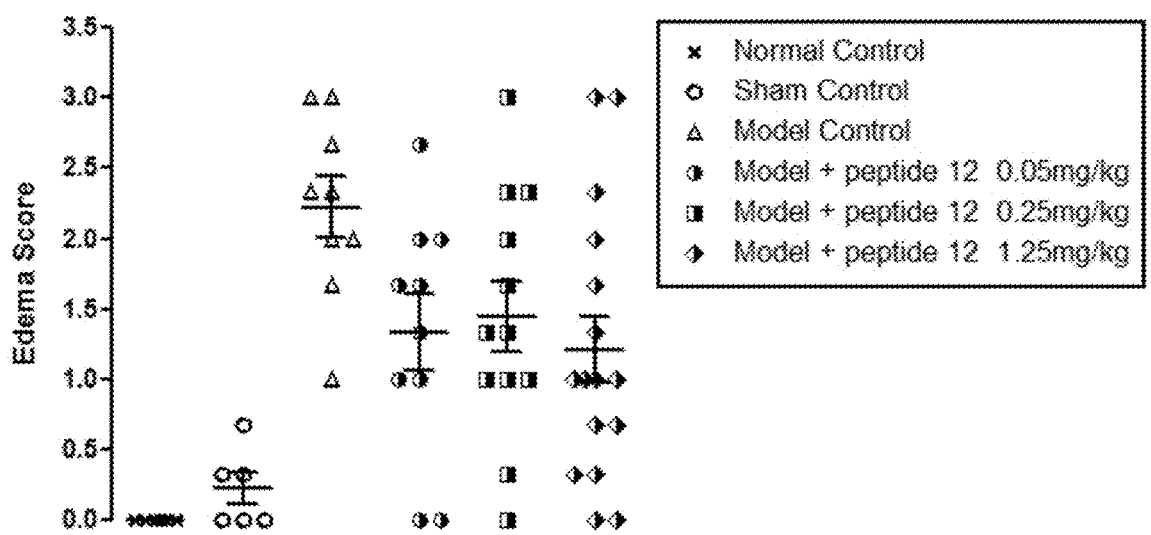
Figure 4. Beneficial effects of peptide No. 12 on the pathologic changes of edema in sodium taurocholate induced pancreatitis model

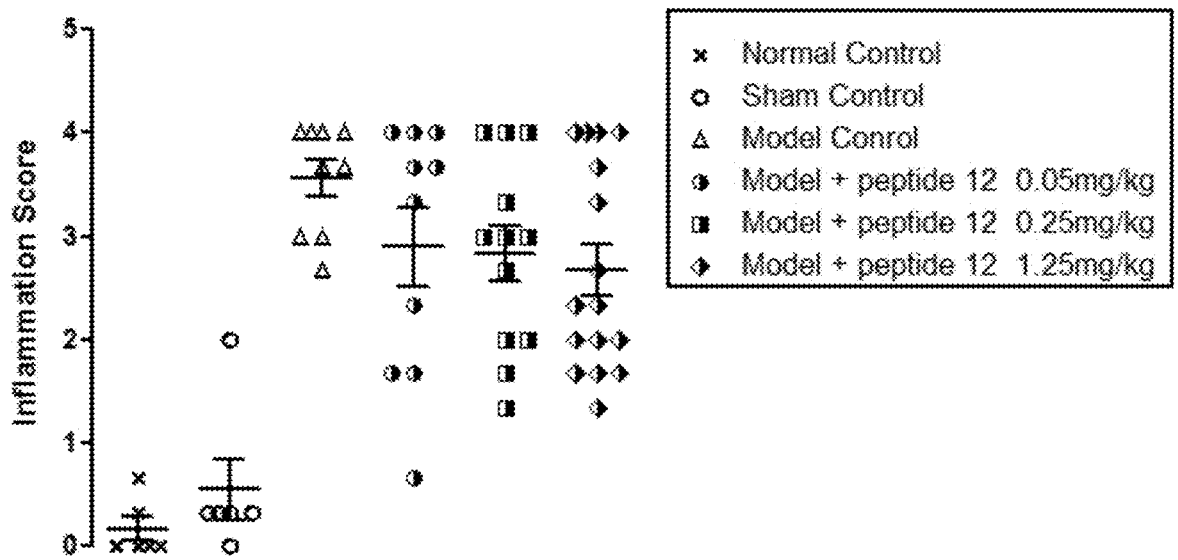
Figure 5. Beneficial effects of peptide No. 12 on the pathologic changes of inflammation in sodium taurocholate induced pancreatitis model
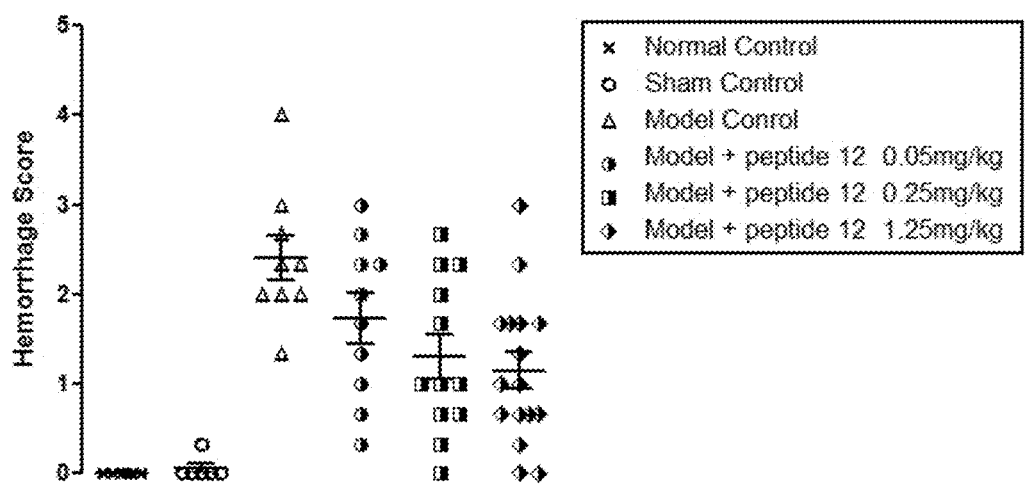
Figure 6. Beneficial effects of peptide No. 12 on the pathologic changes of hemorrhage in sodium taurocholate induced pancreatitis model

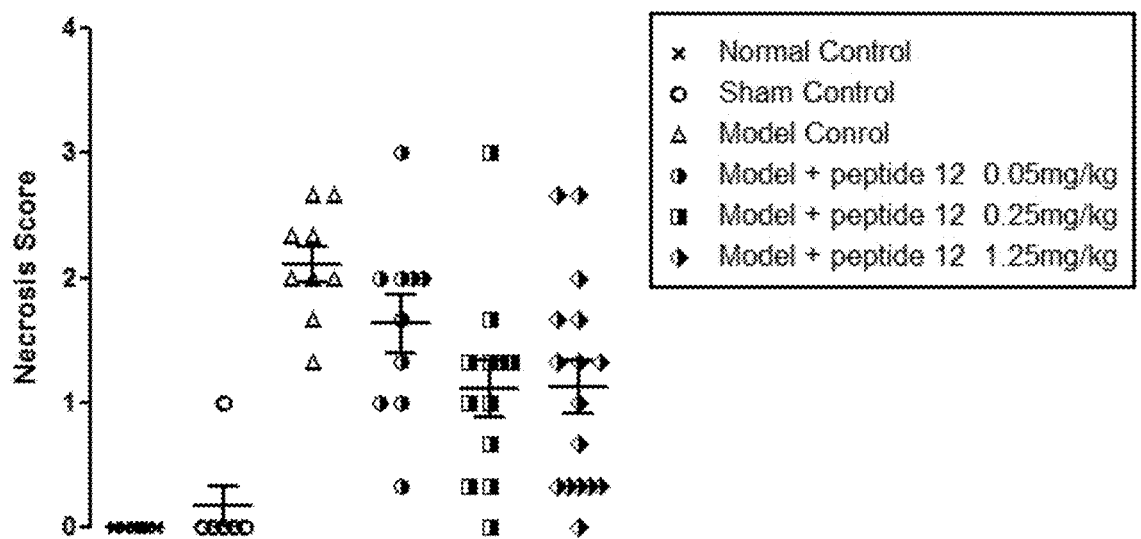
Figure 7. Beneficial effects of peptide No. 12 on the pathologic changes of necrosis in sodium taurocholate induced pancreatitis model
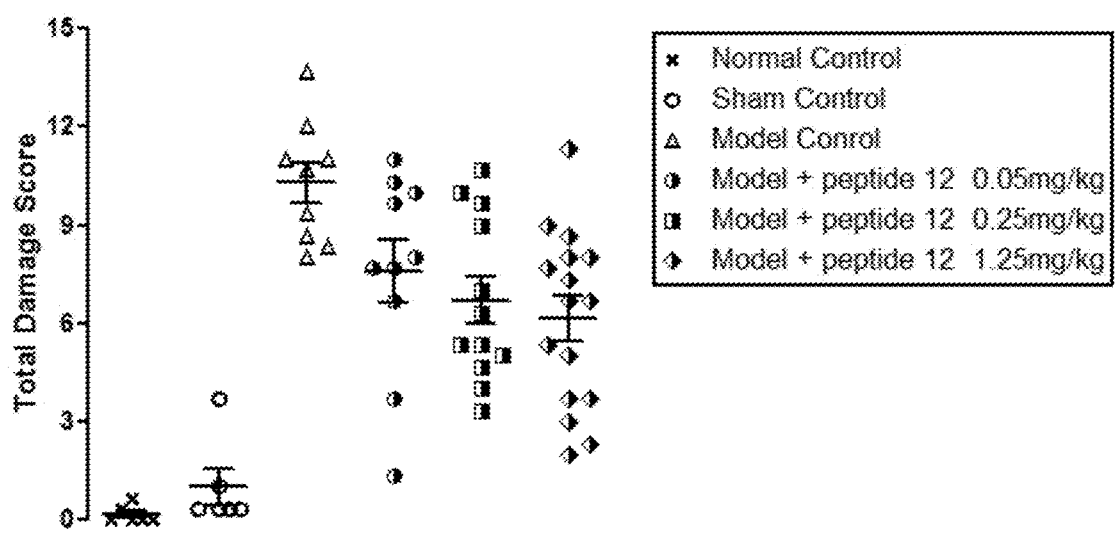
Figure 8. Beneficial effects of peptide No. 12 on the pathologic changes of total damage in sodium taurocholate induced pancreatitis model

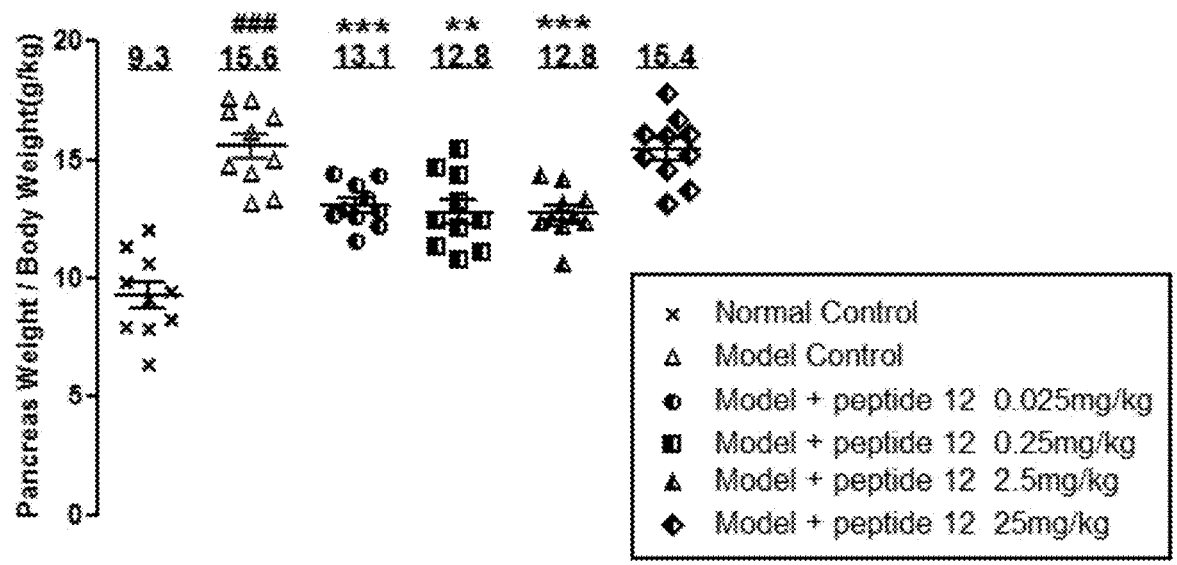
Figure 9. Beneficial effects of peptide No. 12 on the pancreatic index in caerulein induced pancreatitis model
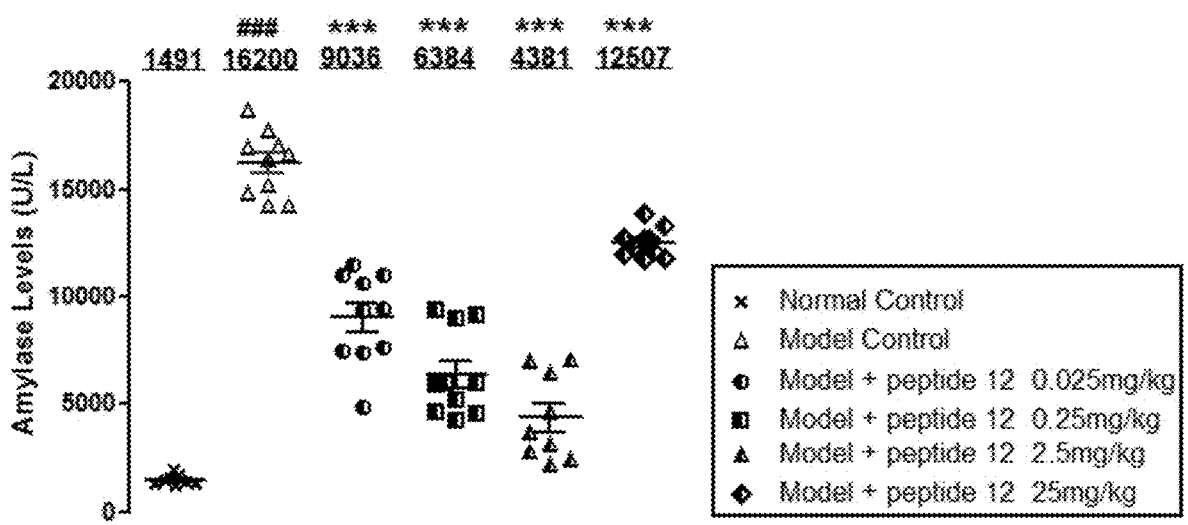
Figure 10. Beneficial effects of peptide No. 12 on the serum amylase levels in caerulein induced pancreatitis model

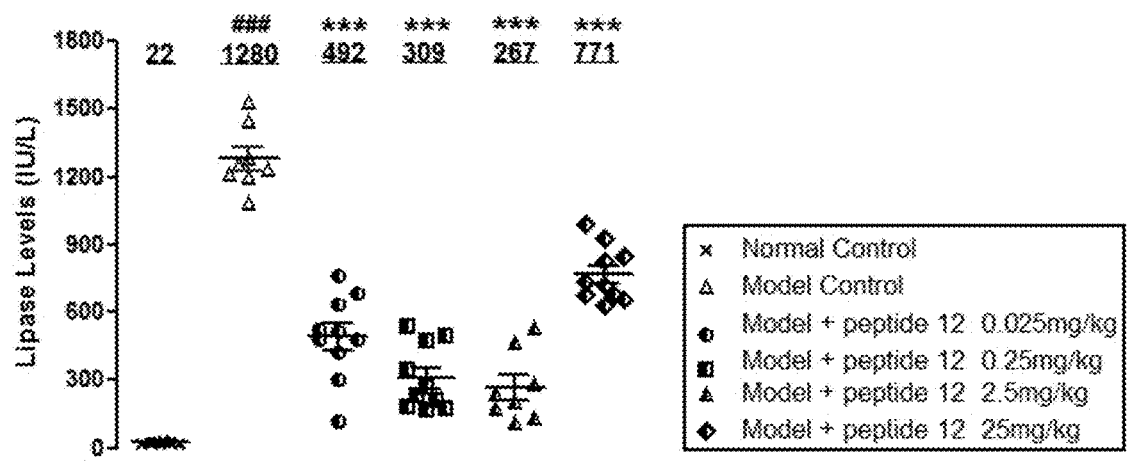
Figure 11. Beneficial effects of peptide No. 12 on the serum lipase levels in caerulein induced pancreatitis model
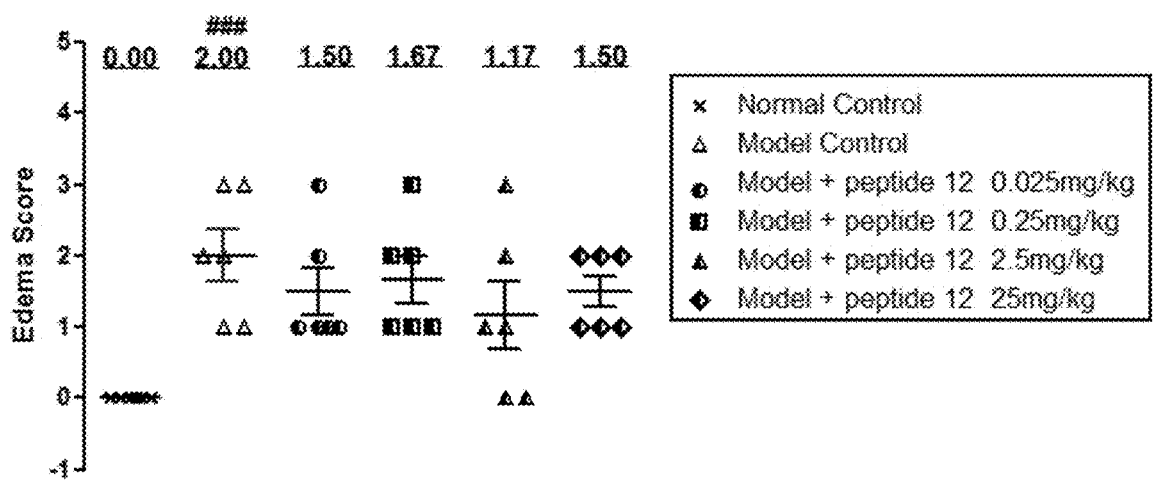
Figure 12. Beneficial effects of peptide No. 12 on the pathologic change of edema in caerulein induced pancreatitis model

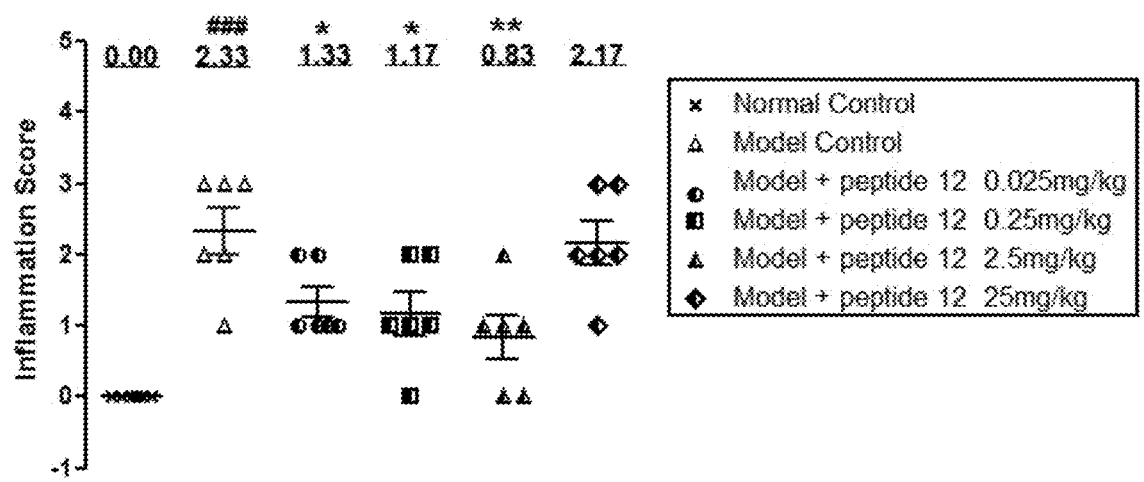
Figure 13. Beneficial effects of peptide No. 12 on the pathologic change of inflammation in caerulein induced pancreatitis model

USE OF PEPTIDE COMPOUNDS IN TREATING ACUTE PANCREATITIS

PRIORITY CLAIMS AND RELATED APPLICATIONS

This application is the U.S. national phase of and claims priority to PCT/CN2017/084013, filed Nov. 5, 2017, the entire content of each of which is incorporated herein by reference.

TECHNICAL FIELD

The invention generally relates to the field of peptide compounds for treating acute pancreatitis, and more specifically to the use of INGAP-PP peptide, HIP peptide, or analogs thereof in treating acute pancreatitis.

BACKGROUND OF THE INVENTION

Pancreatitis is generally considered as a disease of the pancreas caused by the digestion of trypsin itself. Based on the course of the disease, pancreatitis can be divided into acute pancreatitis (AP) and chronic pancreatitis (CP). The annual occurrence of pancreatitis is reported to be 13-45/100,000, and the occurrence of acute pancreatitis has been increasing over the past 30 years.

Acute pancreatitis is a disease of multiple organ dysfunction involving a variety of factors. Its typical symptoms include severe and persistent upper abdominal pain, which usually radiates to the back and ribs, and is often accompanied by vomiting, abdominal distention, fever, increased heart rate, increased white blood cell count, elevated blood or urinary amylase levels. Interstitial edema and fat necrosis to macroscopic pancreatic parenchyma or peripancreatic necrosis and hemorrhage can be seen from microscopic observation. The causes and pathogenesis of acute pancreatitis vary, and various etiologies and mechanisms may interact, leading to poor clinical prognosis.

At present, the existing treatment methods are limited to supportive and conservative treatments including pain relief, fluid replacement to maintain water and electrolyte balance, nutritional support, infection prevention and prevention of complications. There is no drug proven to have significant efficacy in curing acute pancreatitis.

Therefore, it is still necessary to develop new drugs and methods that can effectively treat acute pancreatitis.

SUMMARY OF INVENTION

The diagnostic criteria of acute pancreatitis are basically the same as an international consensus. It is considered that the diagnosis of acute pancreatitis should meet at least two of the following three criteria: (1) abdominal pain symptoms consistent with acute pancreatitis; (2) serum amylase and/or lipase ≥3 times the upper limit of their normal values; and (3) imaging characteristics of acute pancreatitis.

The applicant unexpectedly found that INGAP-PP peptide, HIP peptide, or their analogs may significantly reduce the elevation of blood amylase and lipase levels caused by pancreatitis, lower the degree of pancreatic pathological damage caused by pancreatitis, and significantly improve the survival rate of animal models of acute pancreatitis induced by sodium taurocholate.

Therefore, in some respects, this invention provides the use of INGAP-PP peptide, HIP peptide, or analogs thereof in the treatment of acute pancreatitis.

In other respects, the invention provides a method of treating acute pancreatitis, including administering a patient a composition comprising an INGAP-PP peptide, HIP peptide, or analogs thereof.

These and other aspects, features and advantages of the disclosure will become apparent in accordance with the following description of the disclosure and in conjunction with the drawings.

BRIEF DESCRIPTION OF THE DRAWINGS

In conjunction with the drawings, the above and other features, aspects and advantages of the disclosure herein will be readily understood from the following description:

FIG. 1 shows the comparison of the survival rate between the peptide treatment groups and the model control group in sodium taurocholate-induced severe acute pancreatitis (SAP) model.

FIG. 2 shows the comparison of the serum amylase levels between the peptide treatment groups and the model control group in sodium taurocholate-induced severe acute pancreatitis (SAP) model.

FIG. 3 shows the comparison of the serum lipase levels between the peptide treatment groups and the model control group in sodium taurocholate-induced severe acute pancreatitis (SAP) model.

FIG. 4 shows the comparison of pathological changes of edema between the peptide treatment groups and the model control group in sodium taurocholate-induced severe acute pancreatitis (SAP) model.

FIG. 5 shows the comparison of pathological changes of inflammation between the peptide treatment groups and the model control group in sodium taurocholate-induced severe acute pancreatitis (SAP) model.

FIG. 6 shows the comparison of pathological changes of hemorrhage between the peptide treatment groups and the model control group in sodium taurocholate-induced severe acute pancreatitis (SAP) model.

FIG. 7 shows the comparison of pathological changes of necrosis between the peptide treatment groups and the model control group in sodium taurocholate-induced severe acute pancreatitis (SAP) model.

FIG. 8 shows the comparison of pathological changes of total damage between the peptide treatment groups and the model control group in sodium taurocholate-induced severe acute pancreatitis (SAP) model.

FIG. 9 shows the comparison of pancreatic index between the peptide treatment groups and the model control group in caerulein-induced acute pancreatitis (AP) model.

FIG. 10 shows the comparison of amylase levels between the peptide treatment groups and the model control group in caerulein-induced acute pancreatitis (AP) model.

FIG. 11 shows the comparison of lipase levels between the peptide treatment groups and the model control group in caerulein-induced acute pancreatitis (AP) model.

FIG. 12 shows the comparison of pathological changes of edema between the peptide treatment groups and the model control group in caerulein-induced acute pancreatitis (AP) model.

FIG. 13 shows the comparison of pathological changes of inflammation between the peptide treatment groups and the model control group in caerulein-induced acute pancreatitis (AP) model.

DETAILED DESCRIPTION OF THE INVENTION

Each of the embodiments provided below contributes to the interpretation of certain aspects of the disclosure herein, but should not be construed as limiting the scope of the invention. In addition, throughout the Description of the Invention and Claims, as used herein, similar language may be applied to modify any quantitative representation that allows for changes, but will not lead to changes in the related basic functions. Thus, the value modified by one or more terms such as "approximate" is not limited to the specified exact value. In some cases, the similar language may correspond to the precision of the instrument used to measure the value.

The phrases "parenteral administration" and "non-gastrointestinal administration" are well-known terms in the field, including modes of administration other than intestinal and local administration, such as injections, but not limited to injection and infusion via intravenous, intramuscular, intrapleural, intravascular, intrapericardial, arterial, intrathecal, intracapsular, intraorbital, intracardiac, intradermal, intraperitoneal, tracheal, subcutaneous, subepidermal, intraarticular, subcapsular, subarachnoid, spinal, and sternum.

The term "treatment" includes preventing the occurrence of disease, disorder or symptom in an animal that may be susceptible to disease, disorder and/or condition but has not yet been diagnosed; inhibiting disease, disorder or symptom, such as impeding its development; and alleviating disease, disorder or symptom, such as subsiding the disease, disorder, and/or symptom of the disease. Treatment of diseases or symptom includes the improvement of specific disease or at least one specific symptom of the disease.

The phrase "pharmaceutically acceptable" refers to compositions, polymers, and other materials and/or dosage forms that are within reasonable medical judgment applicable to contact with human and animal tissues without excessive toxicity, irritation, allergy or other problems or complications.

The phrase "pharmaceutically acceptable carrier" refers to a pharmaceutically acceptable material, composition or medium, such as a liquid or solid filler, diluent, solvent, or encapsulation material, involved in carrying or transporting any test composition from one organ or part of the body to another. It must be "acceptable" in the sense that it is compatible with other components of the test composition and does not harm the patient.

As used herein, the term "patient" refers to a mammal, such as a mouse, guinea pig, rat, dog or human. A preferred patient is a human.

The preparations of certain INGAP-PP peptide, HIP peptide and their analogs were disclosed in PCT/CN2014/073483 and PCT/CN2013/072771, previously submitted by this applicant, indicating that certain INGAP-PP peptide, HIP peptide, and their analogs have multiple pharmacological activities, but anti-acute pancreatitis activities were not disclosed. PCT/CN2014/073483 and PCT/CN2013/072771 are both integrated herein in their entireties by reference.

The applicant unexpectedly discovered that certain INGAP-PP peptide, HIP peptide, and their analog (as exemplified by Ac-IGLHD PSHGT LPAGS-OH, SEQ ID NO. 12 in Table 2 below), significantly reduced the pathological changes of pancreatic edema and inflammation, and significantly reduced the levels of blood amylase and lipase (see FIG. 10 and FIG. 11) in a mouse model of acute pancreatitis induced by caerulein. Administrated with certain INGAP-PP peptide, HIP peptide, and their analog (as exemplified by Ac-IGLHD PSHGT LPAGS-OH, SEQ ID NO. 12 in Table 2 below) can significantly increase the survival rate of rats with acute pancreatitis induced by sodium taurocholate. In Example 1, three doses (low dose of 0.05 mg/kg, medium dose of 0.25 mg/kg and high dose of 1.25 mg/kg) were tested. All the surviving animals in the treatment groups maintained good mental status and activity status, which were significantly better than those in the model control group.

Therefore, in one aspect, the application provides the use of INGAP-PP peptide, HIP peptide or their analogs in the treatment of patients with acute pancreatitis. The application also provides the use of INGAP-PP peptide, HIP peptide or their analogs in the preparation of medicament for the treatment of acute pancreatitis. In one embodiment, the INGAP-PP peptide analog is Ac-IGLHD PSHGT LPAGS-OH (SEQ ID NO: 12).

INGAP-PP peptide, HIP peptide and their analogs are provided in Table 1 to Table 3 below.

TABLE 1

INGAP-PP and HIP Peptides

| Peptide ID/<br>SEQ ID NO. | Sequence |
|---|---|
| 1 (INGAP-PP) | H-IGLHDPSHGTLPNGS-OH |
| 2 (HIP) | H-IGLHDPTQGTEPNGE-OH |

TABLE 2

Exemplary INGAP-PP Analogs

| | |
|---|---|
| 1 | H-IGLHDPSHGTLPNGS-OH |
| 6 | H-IGLHAPSHGTLPNGS-OH |
| 7 | H-IGLHDPSHGTLPAGS-OH |
| 8 | H-IGLHAPSHGTLPAGS-OH |
| 9 | H-IGLHDPSHGTLPAGSK-OH |
| 10 | H-IGLHDPSHGTLP(Aib)GS-OH |
| 11 | H-IGLHDPSHGTLP(N-methyl-L-Alanine)GS-OH |
| 12 | Ac-IGLHDPSHGTLPAGS-OH |
| 13 | H-(D-Isoleucine)GLHDPSHGTLPAGS-OH |
| 14 | H-(L-NorValine)GLHDPSHGTLPAGS-OH |
| 15 | H-(L-NorLeucine)GLHDPSHGTLPAGS-OH |
| 16 | Ac-IGLHDPSHGTLPNGS-OH |
| 17 | H-(D-Isoleucine)GLHDPSHGTLPNGS-OH |
| 18 | H-IGLHDPSHGTEPNGS-OH |
| 19 | H-IGLHDPSQGTLPNGS-OH |
| 20 | H-IGLHDPTHGTLPNGS-OH |
| 21 | H-IGLHDPSHGTLPNGE-OH |
| 22 | H-IGLHDPSHGTLPNGK-OH |
| 23 | H-IGLHDPSHGTLPAGK-OH |
| 24 | H-IGLHDPSHGTEPAGS-OH |
| 25 | H-IGLHDPSQGTLPAGS-OH |
| 26 | H-IGLHDPTHGTLPAGS-OH |
| 27 | H-IGLHDPSHGTLPAGE-OH |

TABLE 2-continued

Exemplary INGAP-PP Analogs

| | |
|---|---|
| 28 | H-IGLHDPSHGTLPAG-NH2 |
| 29 | Ac-IGLHDPSHGTLPAGS-NH2 |
| 30 | Ac-IGLHDPSHGTLPAG-NH2 |
| 31 | Ac-IGLHDPSHGTLPNGS-NH2 |
| 32 | H-IGLHDPSHGTLPNGS-NH2 |
| 33 | H-IGLHDPSHGTLPNGSC-OH |
| 34 | Ac-IGLHDPSHGTLPNGSC-OH |
| 35 | H-IGLHDPSHGTLPNGSC-NH2 |
| 36 | Ac-IGLHDPSHGTLPNGSC-NH2 |
| 37 | H-IGLHDPSHGTLPNGC-OH |
| 38 | Ac-IGLHDPSHGTLPNGC-OH |
| 39 | H-IGLHDPSHGTLPNGC-NH2 |
| 40 | Ac-IGLHDPSHGTLPNGC-NH2 |
| 41 | H-IGLHDPSHGTLPAGS-NH2 |
| 42 | H-IGLHDPSHGTLPAGSC-OH |
| 43 | Ac-IGLHDPSHGTLPAGSC-OH |
| 44 | H-IGLHDPSHGTLPAGSC-NH2 |
| 45 | Ac-IGLHDPSHGTLPAGSC-NH2 |
| 46 | H-IGLHDPSHGTLPAGC-OH |
| 47 | Ac-IGLHDPSHGTLPAGC-OH |
| 48 | H-IGLHDPSHGTLPAGC-NH2 |
| 49 | Ac-IGLHDPSHGTLPAGC-NH2 |
| 73 | IGLHDPSHGTLPAG |
| 74 | IGLHDPSHGTLPNG |
| 75 | Ac-IGLHDPSHGTLPNG |
| 76 | IGLHDPSHGTLPNG-NH2 |
| 77 | Ac-IGLHDPSHGTLPNG-NH2 |
| 78 | H-IGLHDPSHGTLPQGS-OH |
| 79 | H-IGLHDPSHGTLPDGS-OH |
| 80 | H-IGLHDPSHGTLPEGS-OH |
| 81 | H-IGLHEPSHGTLPNGS-OH |
| 82 | H-IGLHQPSHGTLPNGS-OH |
| 83 | H-IGLHNPSHGTLPNGS-OH |
| 84 | H-IGLHEPSHGTLPAGS-OH |
| 85 | H-IGLHQPSHGTLPAGS-OH |
| 86 | H-IGLHNPSHGTLPAGS-OH |
| 87 | H-IGLHDPSHGTLPQGSC-OH |
| 88 | H-IGLHDPSHGTLPDGSC-OH |
| 89 | H-IGLHDPSHGTLPEGSC-OH |
| 90 | H-IGLHEPSHGTLPNGSC-OH |
| 91 | H-IGLHQPSHGTLPNGSC-OH |
| 92 | H-IGLHNPSHGTLPNGSC-OH |
| 93 | H-IGLHDPSHGTLPQG-OH |
| 94 | H-IGLHDPSHGTLPDG-OH |
| 95 | H-IGLHDPSHGTLPEG-OH |
| 96 | H-IGLHEPSHGTLPNG-OH |
| 97 | H-IGLHQPSHGTLPNG-OH |
| 98 | H-IGLHNPSHGTLPNG-OH |
| 99 | H-IGLHEPSHGTLPAG-OH |
| 100 | H-IGLHQPSHGTLPAG-OH |
| 101 | H-IGLHNPSHGTLPAG-OH |
| 102 | H-IGLHDPSHGTLPQGE-OH |
| 103 | H-IGLHDPSHGTLPDGE-OH |
| 104 | H-IGLHDPSHGTLPEGE-OH |
| 105 | H-IGLHEPSHGTLPNGE-OH |
| 106 | H-IGLHQPSHGTLPNGE-OH |
| 107 | H-IGLHNPSHGTLPNGE-OH |
| 108 | H-IGLHEPSHGTLPAGE-OH |
| 109 | H-IGLHQPSHGTLPAGE-OH |
| 110 | H-IGLHNPSHGTLPAGE-OH |

TABLE 3

Exemplary HIP Analogs

| Peptide ID/ SEQ ID NO. | Sequence |
|---|---|
| 2 | H-IGLHDPTQGTEPNGE-OH |
| 50 | H-IGLHDPTQGTEPAGE-OH |
| 51 | H-IGLHDPTQGTEP(Aib)GE-OH |
| 52 | Ac-IGLHDPTQGTEPAGE-OH |
| 53 | H-(D-Isoleucine)GLHDPTQGTEPAGE-OH |
| 54 | Ac-IGLHDPTQGTEPNGE-OH |
| 55 | H-(D-Isoleucine)GLHDPTQGTEPNGE-OH |
| 56 | H-IGLHDPTQGTEPNGS-OH |
| 57 | H-IGLHDPTQGTEPAGS-OH |
| 58 | H-IGLHDPTQGTLPNGE-OH |
| 59 | H-IGLHDPTQGTLPAGE-OH |
| 60 | Ac-IGLHDPTQGTEPAG-NH$_2$ |
| 61 | Ac-IGLHDPTQGTEPNGE-NH$_2$ |

TABLE 3-continued

Exemplary HIP Analogs

| Peptide ID/ SEQ ID NO. | Sequence |
|---|---|
| 62 | Ac-IGLHDPTQGTEPAGE-NH$_2$ |
| 63 | H-IGLHDPTQGTEPNGE-NH$_2$ |
| 64 | H-IGLHDPTQGTEPNGC-OH |
| 65 | Ac-IGLHDPTQGTEPNGC-OH |
| 66 | H-IGLHDPTQGTEPNGC-NH$_2$ |
| 67 | Ac-IGLHDPTQGTEPNGC-NH$_2$ |
| 68 | H-IGLHDPTQGTEPAGE-NH$_2$ |
| 69 | H-IGLHDPTQGTEPAGC-OH |
| 70 | Ac-IGLHDPTQGTEPAGC-OH |
| 71 | H-IGLHDPTQGTEPAGC-NH$_2$ |
| 72 | Ac-IGLHDPTQGTEPAGC-NH$_2$ |

As is well known to those skilled in the art, in the peptide sequence, the symbols and the amino acids they represent are shown in Table 4 below.

TABLE 4

| Chinese Name | English Name | Symbols or Abbreviations |
|---|---|---|
| 丙氨酸 | Alanine | A or Ala |
| 精氨酸 | Arginine | R or Arg |
| 天冬酰胺 | Asparagine | N or Asn |
| 天冬氨酸 | Aspartic acid | D or Asp |
| 半胱氨酸 | Cysteine | C or Cys |
| 谷氨酰胺 | Glutamine | Q or Gln |
| 谷氨酸 | Glutamic acid | E or Glu |
| 甘氨酸 | Glycine | G or Gly |
| 组氨酸 | Histidine | H or His |
| 异亮氨酸 | Isoleucine | I or Ile |
| 亮氨酸 | Leucine | L or Leu |
| 赖氨酸 | Lysine | K or Lys |
| 蛋氨酸 | Methionine | M or Met |
| 苯丙氨酸 | Phenylalanine | F or Phe |
| 脯氨酸 | Proline | P or Pro |
| 丝氨酸 | Serine | S or Ser |
| 苏氨酸 | Threonine | T or Thr |
| 色氨酸 | Tryptophan | W or Trp |
| 酪氨酸 | Tyrosine | Y or Tyr |
| 缬氨酸 | Valine | V or Val |

In one embodiment, the INGAP-PP peptide analogs comprise the following general formula.

(1)
(SEQ ID NO: 111)
$X^1GLHX^2PX^3X^4GTX^5PX^6GS$;

wherein, $X^1$ is selected from Isoleucine (I), D-Isoleucine, L-NorValine or L-NorLeucine; $X^2$ is selected from Alanine (A) or Aspartic Acid (D); $X^3$ is selected from Serine (S) or Threonine (T); $X^4$ is selected from Histidine (H) or Glutamine (Q); $X^5$ is selected from Leucine (L) or Glutamic acid (E); and when it is established that $X^1$ is Isoleucine (I), $X^2$ is Aspartic Acid (D), $X^3$ is Serine (S), $X^4$ is Histidine (H), and $X^5$ is Leucine (L), then $X^6$ is selected from either Alanine (A), α-Amino-isobutyric acid or N-methyl-L-Alanine; and when it is not established that $X^1$ is Isoleucine (I), $X^2$ is Aspartic Acid (D), $X^3$ is Serine (S), $X^4$ is Histidine (H) and $X^5$ is Leucine (L), then $X^6$ is selected from Alanine (A), Asparagine (N), α-Amino-isobutyric acid or N-methyl-L-Alanine.

In one embodiment, the INGAP-PP peptide analogs of formula (1) can be selected from the following peptides.

(SEQ ID NO: 6)
H-IGLHAPSHGTLPNGS-OH;

(SEQ ID NO: 10)
H-IGLHDPSHGTLP(Aib)GS-OH;

(SEQ ID NO: 11)
H-IGLHDPSHGTLP(N-methyl-L-Alanine)GS-OH;

(SEQ ID NO: 17)
H-(D-Isoleucine)GLHDPSHGTLPNGS-OH;

(SEQ ID NO: 18)
H-IGLHDPSHGTEPNGS-OH;

(SEQ ID NO: 19)
H-IGLHDPSQGTLPNGS-OH;
and (SEQ ID NO: 20)
H-IGLHDPTHGTLPNGS-OH.

In another embodiment, the INGAP-PP peptide analogs of formula (1) can be selected from the following peptides.

(SEQ ID NO: 7)
H-IGLHDPSHGTLPAGS-OH;

(SEQ ID NO: 8)
H-IGLHAPSHGTLPAGS-OH;

(SEQ ID NO: 13)
H-(D-Isoleucine)GLHDPSHGTLPAGS-OH;

(SEQ ID NO: 14)
H-(L-NorValine)GLHDPSHGTLPAGS-OH;

(SEQ ID NO: 15)
H-(L-NorLeucine)GLHDPSHGTLPAGS-OH;

(SEQ ID NO: 24)
H-IGLHDPSHGTEPAGS-OH;

(SEQ ID NO: 25)
H-IGLHDPSQGTLPAGS-OH;
and (SEQ ID NO: 26)
H-IGLHDPTHGTLPAGS-OH.

In another embodiment, the INGAP-PP peptide analogs comprise the following general formula.

(2)
(SEQ ID NO: 112)
$R^1$-IGLHDPSHGTLPNGX$^1$(C)$_m$-R$^2$;

wherein, m is 0 or 1; $R^1$ is selected from —H or —Ac; $R^2$ is selected from —OH or —NH$_2$; and when it is established that $R^1$ is —H, $R^2$ is —OH and m is 0, then $X^1$ is selected from Glutamic acid (E), Cysteine (C) or Lysine (K); and when it is not established that R¹ is —H, R² is —OH and m is 0, then X¹ is selected from Serine (S), Glutamic acid (E), Cysteine (C) or Lysine (K).

In one embodiment, the INGAP-PP peptide analogs in formula (2) can be selected from H-IGLHDPSHGTLPNGE-OH (SEQ ID NO:21) and H-IGLHDPSHGTLPNGK-OH (SEQ ID NO: 22).

In one embodiment, the INGAP-PP peptide analogs in formula (2) can be selected from the following peptides.

```
                                        (SEQ ID NO: 31)
    Ac-IGLHDPSHGTLPNGS-NH₂;

(SEQ ID NO: 32)
    H-IGLHDPSHGTLPNGS-NH₂;
    and (SEQ ID NO: 16)
    Ac-IGLHDPSHGTLPNGS-OH.
```

In one embodiment, the INGAP-PP peptide analogs in formula (2) can be selected from the following peptides.

```
                                        (SEQ ID NO: 37)
    H-IGLHDPSHGTLPNGC-OH;

(SEQ ID NO: 38)
    Ac-IGLHDPSHGTLPNGC-OH;

(SEQ ID NO: 39)
    H-IGLHDSHGTLPNGC-NH₂;
    and (SEQ ID NO: 40)
    Ac-IGLHDPSHGTLPNGC-NH₂.
```

In one embodiment, the INGAP-PP peptide analogs in formula (2) can be selected from the following peptides.

```
                                        (SEQ ID NO: 33)
    H-IGLHDPSHGTLPNGSC-OH;

(SEQ ID NO: 34)
    Ac-IGLHDPSHGTLPNGSC-OH);

(SEQ ID NO: 35)
    H-IGLHDPSHGTLPNGSC-NH₂;
    and (SEQ ID NO: 36)
    Ac-IGLHDPSHGTLPNGSC-NH₂.
```

In one embodiment, the INGAP-PP peptide analogs in formula (2) can be selected from the following peptides.

```
                                        (SEQ ID NO: 74)
    H-IGLHDPSHGTLPNG-OH;

(SEQ ID NO: 75)
    Ac-IGLHDPSHGTLPNG-OH;

(SEQ ID NO: 76)
    H-IGLHDPSHGTLPNG-NH₂;
    and (SEQ ID NO: 77)
    Ac-IGLHDPSHGTLPNG-NH₂.
```

In another embodiment, the INGAP-PP peptide analogs comprise the following general formula.

(3)
```
                                        (SEQ ID NO: 113)
    R¹-IGLHDPSHGTLPAG(X¹)ₘ-R²;
``` wherein, m is 0 or 1; R¹ is selected from —H or —Ac; R² is selected from —OH or —NH₂; and when it is established that R¹ is —H, R² is —OH and m is 1, then X¹ is selected from Glutamic acid (E), Cysteine (C) or Lysine (K); and when it is not established that R¹ is —H, R² is —OH and m is 1, then X¹ is selected from Serine (S), Glutamic acid (E), Cysteine (C) or Lysine (K).

In one embodiment, the INGAP-PP peptide analogs of formula (3) can be selected from H-IGLHDPSHGTLPAGE-OH (SEQ ID NO: 27) and H-IGLHDPSHGTLPAGK-OH (SEQ ID NO: 23).

In one embodiment, the INGAP-PP peptide analogs of formula (3) can be selected from the following peptides.

```
                                        (SEQ ID NO: 29)
    Ac-IGLHDPSHGTLPAGS-NH₂;

(SEQ ID NO: 41)
    H-IGLHDPSHGTLPAGS-NH₂;
    and (SEQ ID NO: 12)
    Ac-IGLHDPSHGTLPAGS-OH.
```

In one embodiment, the INGAP-PP peptide analogs of formula (3) can be selected from the following peptides.

```
                                        (SEQ ID NO: 46)
    H-IGLHDPSHGTLPAGC-OH;

(SEQ ID NO: 47)
    Ac-IGLHDPSHGTLPAGC-OH;

(SEQ ID NO: 48)
    H-IGLHDPSHGTLPAGC-NH₂;
    and (SEQ ID NO: 49)
    Ac-IGLHDPSHGTLPAGC-NH₂.
```

In one embodiment, the INGAP-PP peptide analogs of formula (3) can be selected from the following peptides.

```
                                        (SEQ ID NO: 73)
    H-IGLHDPSHGTLPAG-OH;

(SEQ ID NO: 28)
    H-IGLHDPSHGTLPAG-NH₂;
    and (SEQ ID NO: 30)
    Ac-IGLHDPSHGTLPAG-NH₂.
```

In one embodiment, the INGAP-PP peptide analogs comprise the following general formula.

(4)
```
                                        (SEQ ID NO: 114)
    R¹-IGLHDPSHGTLPAGSX²-R²;
``` wherein, X² is selected from Lysine (K) or Cysteine (C); R¹ is selected from —H or —Ac, R² is selected from —OH or —NH₂.

In one embodiment, the INGAP-PP peptide analogs of formula (4) can be selected from the following peptides.

H-IGLHDPSHGTLPAGSK-OH; (SEQ ID NO: 9)

H-IGLHDPSHGTLPAGSC-OH; (SEQ ID NO: 42)

Ac-IGLHDPSHGTLPAGSC-OH; (SEQ ID NO: 43)

H-IGLHDPSHGTLPAGSC-NH$_2$; and (SEQ ID NO: 44)

Ac-IGLHDPSHGTLPAGSC-NH$_2$. (SEQ ID NO: 45)

In one embodiment, the HIP peptide analogs comprise the following general formula.

$$X^1GLHDPTQGTX^2PX^3GE; \quad (5) \quad (SEQ\ ID\ NO:\ 115)$$

wherein, $X^1$ is selected from Isoleucine (I) or D-Isoleucine; $X^2$ is selected from Glutamic acid (E) or Leucine (L); and when it is established that $X^1$ is Isoleucine (I) and $X^2$ is Glutamic acid (E), then $X^3$ is selected from Alanine (A) or α-Amino-isobutyric acid; and when it is not established that $X^1$ is Isoleucine (I) and $X^2$ is Glutamic acid (E), then $X^3$ is selected from Alanine (A), Asparagine (N) or α-Amino-isobutyric acid.

In one embodiment, the HIP peptide analogs of formula (5) can be selected from the following peptides.

H-IGLHDPTQGTEP(Aib)GE-OH; (SEQ ID NO: 51)

H-(D-Isoleucine)GLHDPTQGTEPNGE-OH; and (SEQ ID NO: 55)

H-IGLHDPTQGTLPNGE-OH. (SEQ ID NO: 58)

In one embodiment, the HIP peptide analogs of formula (5) can be selected from the following peptides.

H-IGLHDPTQGTEPAGE-OH; (SEQ ID NO: 50)

H-(D-Isoleucine)GLHDPTQGTEPAGE-OH; and (SEQ ID NO: 53)

H-IGLHDPTQGTLPAGE-OH. (SEQ ID NO: 59)

In one embodiment, the HIP peptide analogs comprise the following general formula.

$$R^1\text{-}IGLHDPTQGTEPNGX^1\text{-}R^2; \quad (6) \quad (SEQ\ ID\ NO:\ 116)$$

wherein, $R^1$ is selected from —H or —Ac; $R^2$ is selected from —OH or —NH$_2$; and when it is established that $R^1$ is —H and $R^2$ is —OH, then $X^1$ is selected from Serine (S) or Cysteine (C); and when it is not established that $R^1$ is —H and $R^2$ is —OH, then $X^1$ is selected from Serine (S), Glutamic acid (E) or Cysteine (C).

In one embodiment, the HIP peptide analogs of formula (6) can be selected from the following peptides.

Ac-IGLHDPTQGTEPNGE-OH; (SEQ ID NO: 54)

Ac-IGLHDPTQGTEPNGE-NH$_2$; and (SEQ ID NO: 61)

H-IGLHDPTQGTEPNGE-NH$_2$. (SEQ ID NO: 63)

In one embodiment, the HIP peptide analogs of formula (6) can be selected from the following peptides.

H-IGLHDPTQGTEPNGS-OH; (SEQ ID NO: 56)

H-IGLHDPTQGTEPNGC-OH; (SEQ ID NO: 64)

Ac-IGLHDPTQGTEPNGC-OH; (SEQ ID NO: 65)

H-IGLHDPTQGTEPNGC-NH$_2$; and (SEQ ID NO: 66)

Ac-IGLHDPTQGTEPNGC-NH$_2$. (SEQ ID NO: 67)

In one embodiment, the HIP peptide analogs comprise the following general formula.

$$R^1\text{-}IGLHDPTQGTEPAG(X^1)_n\text{-}R^2 \quad (7); \quad (SEQ\ ID\ NO:\ 117)$$

wherein, $R^1$ is selected from —H or —Ac; $R^2$ is selected from —OH or —NH$_2$; n is 0 or 1; $X^1$ is selected from Serine (S) or Cysteine (C).

In one embodiment, the HIP peptide analogs of formula (7) can be selected from the following peptides.

H-IGLHDPTQGTEPAGS-OH; (SEQ ID NO: 57)

Ac-IGLHDPTQGTEPAG-NH$_2$; (SEQ ID NO: 60)

H-IGLHDPTQGTEPAGC-OH; (SEQ ID NO: 69)

Ac-IGLHDPTQGTEPAGC-OH; (SEQ ID NO: 70)

H-IGLHDPTQGTEPAGC-NH$_2$; and (SEQ ID NO: 71)

Ac-IGLHDPTQGTEPAGC-NH$_2$. (SEQ ID NO: 72)

In one embodiment, the HIP peptide analogs of formula (7) can be selected from the following peptides.

Ac-IGLHDPTQGTEPAGE-OH; (SEQ ID NO: 52)

Ac-IGLHDPTQGTEPAGE-NH$_2$; and (SEQ ID NO: 62)

H-IGLHDPTQGTEPAGE-NH$_2$. (SEQ ID NO: 68)

The INGAP-PP peptide, HIP peptide, or analogs thereof for the invention can exist in any pharmaceutically acceptable salt form. Especially useful salt forms are acetate and hydrochloride. When the INGAP-PP peptide, HIP peptide, or their analogs of the invention have acid or alkaline group, they can be provided in pharmaceutically acceptable salt form (see, for example, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002).

Suitable acids for the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetylaminobenzoic acid, boric acid, (+)-camphoric acid, camphorsulfonic acid, (+)-(1S)-camphor-10-sulfonic acid, decanoic acid, hexanoic acid, octanoic acid, cinnamic acid, citric acid, cyclic acid, cyclohexyl aminosulfonic acid, dodecyl sulfuric acid, 1,2-ethanedisulfonic acid, ethyl sulfonic acid, 2-hydroxyethyl sulfonic acid, formic acid, fumaric acid, galactose diacid, gentioic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactose acid, lauric acid, maleic acid, (−)-L-malic acid, malonic acid, (±)-DL-mandelic acid, methanesulfonic acid, 2-naphthalene sulfonic acid, 1,5-naphthalene disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, glucaric acid, salicylic acid, 4-aminosalicylic acid, sebacic acid, stearic acid, succinic acid, sulfuric acid, tannic acid, L-tartaric acid, thiocyanic acid, p-toluene sulfonic acid, undecylenic acid and valeric acid.

Suitable bases for the preparation of pharmaceutically acceptable salts include, but are not limited to, inorganic bases such as magnesium hydroxide, calcium hydroxide, potassium hydroxide, zinc hydroxide, or sodium hydroxide; and organic bases such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morphine, 4-(2-hydroxyethyl) morpholine, methylamine, piperidine, piperazine, propylamine, pyrrolidine, 1-(2-hydroxyethyl) pyrrolidine, pyridine, quinuclidine, quinoline, isoquinoline, secondary amine, triethanolamine, trimethylamine, triethylamine, N-methyl-D-glucosamine, 2-amino-2-(hydroxymethyl)-1,3-propanediol, and tromethamine.

The INGAP-PP peptide, HIP peptide, or their analogs of the invention may be combined with pharmaceutically acceptable carriers to prepare compositions for the treatment of acute pancreatitis in patients. Pharmaceutically acceptable carriers may be, for example, water, sodium phosphate buffer solution, phosphate buffered saline solution, normal saline or Ringer solution or other physiological buffer saline, or other solvent or vehicle such as glycol, glycerol, and oil such as olive oil or injectable organic ester.

Pharmaceutically acceptable carriers may include physically acceptable compounds, such as for stabilizing or enhancing the absorption of INGAP-PP peptide, HIP peptide, or their analogs of the invention. These physically acceptable compounds include carbohydrates such as glucose, sucrose or dextrans, etc.; antioxidants such as ascorbic acid or glutathione, etc.; chelating agents such as ethylenediaminetetraacetic acid (EDTA), etc., that can disrupt microbial membranes; divalent metal ions such as calcium or magnesium; low molecular weight proteins; or other stabilizers or excipients. One skilled in the art would know that the choice of pharmaceutically acceptable carriers, including physiologically acceptable compounds, depends, for example, on the route of administration of the composition. Suitable carriers and formulations are well known in the art (see, for example: *Remington: The Science and Practice of Pharmacy,* 19th ed., ed. A. R. Gennaro, Mack Publishing Company, Easton, Pa. (1995); and *Remington's Pharmaceutical Sciences,* 18th ed., Mack Publishing Company, Easton Pa. (1990)). Typically, an appropriate amount of pharmaceutically acceptable salt is used in formulations to render the formulation isotonic. The pH of the solution is generally from about 5 to about 8, for example, from about 7 to about 7.5.

Pharmaceutically acceptable carriers are known to those skilled in the art. These typically would be standard carriers for administration of drugs to humans, including solutions such as sterile water, saline, and buffered solutions at physiological pH, as described above. Pharmaceutical compositions may include carriers, thickeners, diluents, buffers, preservatives, surfactants, and a substance that increases the selection possibility of INGAP-PP peptide, HIP peptide, or their analogs.

Further carriers may include carriers for sustained or controlled release preparations, such as semipermeable matrices of solid hydrophobic polymers covalently or non-covalently bound to the INGAP-PP peptide, HIP peptide or their analogs, which matrices are in the form of shaped articles, for example, films, liposomes, non-liposome lipid complexes or microparticles, and the like, or other biocompatible polymers well known to those skilled in the art (see, for example, U.S. Pat. Nos. 6,824,822 and 8,329,648). Liposomes, which consist of phospholipids or other lipids, are nontoxic, physiologically acceptable and metabolizable carriers that are relatively simple to make and administer. (Gregoriadis, *Liposome Technology*, Vol. 1 (CRC Press, Boca Raton Fla., 1984). Various drug delivery methods are well known to those skilled in the art (Langer, *Nature* 392 (Suppl): 5-10 (1998); Langer et al., *Nature* 428:487-492 (2004)). It will be apparent to those persons skilled in the art that certain carriers can be selected depending upon, for instance, the route of administration and concentration of composition being administered.

The pharmaceutical compositions can be administered in many ways depending on the need for local or systemic treatment and on the area to be treated. It can be understood that various routes of administration are available for INGAP-PP peptide, HIP peptide, or their analogs, and methods of the invention. Such routes of administration encompass systemic and local routes of administration, and include, without limitation, intravenous or intraperitoneal injection, intramuscular injection, subcutaneous injection, transdermal delivery, percutaneous diffusion or electrophoresis, inhalation administration, oral administration, local injection, intracavitary administration, and extended release delivery devices, including local implantation of extended release devices, such as bioerodible or reservoir-based implants. Administration may be topically (ophthalmically, vaginally, rectally, intranasally), orally, by inhalation, or parenterally, for example by intravenous drip, subcutaneous injection, intraperitoneal injection or intramuscular injection.

Preparations for parenteral administration include sterile aqueous solutions or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vechiles include fluid, nutrient replenishers, electrolyte replenishers (such as Ringer's dextrose), and the like. Preservatives and other additives can be present such as, for example, antimicrobials, antioxidants, chelating agents, and inert gases and the like. Insulin is a well known peptide therapeutic, so methods used for delivery of insulin particularly amenable as a delivery method for peptides or analogs of the invention, including but not limited to syringes, pens, infusion pumps, inhalers, mouth sprays, tablets, and the like.

In one aspect, the invention provides a method for treating acute pancreatitis in patients, including administering to the patient a pharmaceutical composition comprising INGAP-PP peptide, HIP peptide, or analogs thereof. In one embodiment, the INGAP-PP peptide analog is Ac-IGLHD PSHGT LPAGS-OH (SEQ ID NO: 12).

In another aspect, the invention provides a method for reducing blood amylase and lipase levels in patients with acute pancreatitis, including administering to the patient a pharmaceutical composition comprising INGAP-PP peptide, HIP peptide, or analogs thereof. In one embodiment, the INGAP-PP peptide analog is Ac-IGLHD PSHGT LPAGS-OH (SEQ ID NO: 12).

In a further aspect, the invention provides a method for treating patient with acute pancreatitis by reducing blood amylase and lipase levels in patients with acute pancreatitis, including administering to the patient a pharmaceutical composition comprising INGAP-PP peptide, HIP peptide, or analogs thereof. In one embodiment, the INGAP-PP peptide analog is Ac-IGLHD PSHGT LPAGS-OH (SEQ ID NO: 12).

In another aspect, the invention provides a method for preventing or reducing pancreatic injury caused by acute pancreatitis, including administering to the patient a pharmaceutical composition comprising INGAP-PP peptide, HIP peptide, or their analogs. In one embodiment, the INGAP-PP peptide analog is Ac-IGLHD PSHGT LPAGS-OH (SEQ ID NO: 12).

In another aspect, the invention provides a method for treating inflammatory pancreatic diseases or symptoms, including administering the patient a pharmaceutical composition containing INGAP-PP peptide, HIP peptide, or analogs thereof. In one embodiment, the INGAP-PP peptide analog is Ac-IGLHD PSHGT LPAGS-OH (SEQ ID NO: 12).

Accordingly, the application also provides the use of pharmaceutical compositions comprising INGAP-PP peptide, HIP peptide, or their analogs in the treatment of patients with acute pancreatitis.

The dosage of INGAP-PP peptide, HIP peptide, or analogs thereof in pharmaceutical compositions can be selected in a broad range, including but not limited to 0.0005 mg/kg/day-100 mg/kg/day; for example, about 0.0005 mg/kg/day, about 0.001 mg/kg/day, about 0.005 mg/kg/day, about 0.01 mg/kg/day, about 0.025 mg/kg/day, about 0.05 mg/kg/day, about 0.1 mg/kg/day, about 0.25 mg/kg/day, about 0.5 mg/kg/day, about 0.75 mg/kg/day, about 1.0 mg/kg/day, about 1.25 mg/kg/day, about 1.50 mg/kg/day, about 1.75 mg/kg/day, about 2.0 mg/kg/day, about 2.5 mg/kg/day, about 5.0 mg/kg/day, about 10.0 mg/kg/day, about 15.0 mg/kg/day, about 25.0 mg/kg/day, about 50.0 mg/kg/day, about 75.0 mg/kg/day, or about 100 mg/kg/day, and the like. The exemplary dose ranges include, but are not limited to 0.0005 mg/kg/day-0.005 mg/kg/day, 0.005 mg/kg/day-0.05 mg/kg/day, 0.025 mg/kg/day-0.25 mg/kg/day, 0.05 mg/kg/day-0.5 mg/kg/day, 0.25 mg/kg/day-2.5 mg/kg/day, 0.5 mg/kg/day-5.0 mg/kg/day, 2.5 mg/kg/day-25.0 mg/kg/day, 5.0 mg/kg/day-50.0 mg/kg/day, or 25.0 mg/kg/day-100 mg/kg/day, and etc.

The INGAP-PP peptide, HIP peptide or analogs thereof of the invention can also be combined with other known or to be developed drugs for the treatment of acute pancreatitis in the same preparation for patients with acute pancreatitis, or different preparations can be administered to patients with acute pancreatitis respectively. Drugs used in combination with INGAP-PP peptide, HIP peptide, or analogs thereof for the treatment of acute pancreatitis include, but are not limited to, trypsin secretion inhibitors such as glucagon, calcitonin, growth inhibitor hormone and it's analog such as octreotide and the like, protease inhibitors such as ulinastatin, gabexate and the like, tumor necrosis factor-alpha (TNF-alpha) inhibitors such as pentoxifylline, and other drugs for treating acute pancreatitis, such as antioxidants, platelet activating factor antagonists, probiotics and activated protein C, etc.

The following examples are intended to illustrate the invention and should not be interpreted in any way as limiting the invention.

Example 1: Effects of Peptide NO. 12 on the Model of Pancreatitis Induced by Sodium Taurocholate After at least 7 days of accumulation period, 60 female and 70 male Sprague-Dawley (SD) rats were included in the study. Five females and eight males were randomly selected as the control group. Another five females and eight males were randomly selected as the sham group, the abdominal cavity was opened for each of the rats in the sham group, and a cotton swab was used to gently flip the duodenum and pancreas, then the abdominal muscle and skin were sutured after the completion of the operation The remaining animals were assigned to establish the severe acute pancreatitis (SAP) rat model using the method of retrograde injection of sodium taurocholate solution with 35 mg/kg dosage into the biliopancreatic duct. The model animals were randomly divided into 4 groups of 24 rats each (male:female=1:1) on the day after model establishment, which were the model control group (vehicle), and low dose group of peptide 12 (0.05 mg/kg), middle dose group of peptide 12 (0.25 mg/kg) and high dose group of peptide 12 (1.25 mg/kg), peptide 12 was dissolved in saline.

The animals were subcutaneously injected once on the day after the establishment of the model, once on the second day, for a total of 2 consecutive days, and the experimental period was 3 days. During the experiment, the animals were observed by cage, including if there is any animal death or near death, mental state, behavioral activities, fecal characteristics, skin, hair, eyes, ears, nose, abdomen, external genitals, anus, limbs, feet, respiration, etc. At the end of the experiment, all the surviving rats were weighed and blood samples were collected to detect the levels of amylase, calcium and lipase in serum of rats in each group. The general anatomical observation was made, focusing on the status of pancreas, gastrointestinal tract, ascites, bile duct obstruction, pulmonary congestion and saponification spots. The pancreas was preserved in 10% formalin fixative for further pathological analysis.

The survival rate of each group was shown in Table 5 and FIG. 1. There was no animal death in normal control group and sham-operated control group, so the survival rate of normal control group and sham control group was 100%. The survival rate of model control group was 37.5%. The survival rate of model animals was improved in all three peptide 12 treatment groups. The improvement of survival rate was related to the dosage of peptide 12, with the animals in the peptide 12 at the dose of 1.25 mg/kg showed the most significant improvement, the survival rate was 66.7% and the survival ratio was 1.78 as compared with the model control group. At the same time, the mental state and activity state of the surviving animals in the peptide 12 treatment groups were significantly better than those in the model control group. The general anatomy of the surviving animals showed that the edema and liquefaction of the pancreas, gastrointestinal obstruction, ascites volume, bile duct obstruction, pulmonary congestion and saponification spots were improved with varying degrees in the peptide 12 treatment groups compared with those in the control group.

TABLE 5

Survival Outcome in Each Group

| Group | Survival Rate | Ratio (treatment group/ model group) |
|---|---|---|
| Normal control | 100% | / |
| Sham control | 100% | / |
| Model control | 37.5% | 1.00 |
| Model + peptide12 0.05 mg/kg | 41.7% | 1.11 |
| Model + peptide 12 0.25 mg/kg | 50.0% | 1.33 |
| Model + peptide 12 1.25 mg/kg | 66.7% | 1.78 |

Compared with normal group and sham-operated group, the levels of amylase and lipase in blood of model control group increased significantly. Compared with model control group, the levels of amylase and lipase in blood of peptide 12 treatment groups decreased (see FIG. 2 and FIG. 3).

The severity of pancreatic injury was assessed by preparing HE slices of pancreas and using Schmidt's scoring standard to evaluate the pathological changes of pancreatic edema, inflammation, hemorrhage and necrosis. The hepatology scoring standard is shown in Table 6 below. The total pancreatic injury calculated as the sum of the above four items.

TABLE 6

Histopathology Scoring Standard

| Pathologic change | Score | | | | |
|---|---|---|---|---|---|
| | 0 | 1 | 2 | 3 | 4 |
| Edema | Absent | Diffuse expansion of inter lobar septae | 1+ diffuse expansion of inter lobular septae | 2+ diffuse expansion of inter acinar septae | 3+ diffuse expansion of inter cellular septaes |
| Inflammation (HPF) | 0~5 intra lobular or perivascular leukocytes | 6~10 intra lobular or perivascular leukocytes | 11~20 intra lobular or perivascular leukocytes | 21~30 intra lobular or perivascular leukocytes | >30% intra lobular or perivascular leukocytes |
| Hemorrhage (HPF) | Absent | 1~3 foci | 4~5 foci | 6~7 foci | >7 foci |
| Area of necrosis | Absent | 1%~10% area | 11%~20% area | 21%~30% area | >30% area |

Note:
1. Microscopic examination of each slide was performed at both low magnification (LPF: ×100) and high magnification (HPF: ×400), and 8 visual fields were randomly selected for observation and grading;
2. Edema and area of necrosis were scoring under low magnification;
3. Inflammation, hemorrhage and necrosis cells were scoring under high magnification.

Pathological scores are shown in tables 7 and in FIG. 4-8.

TABLE 7

Pathological scores of each group

| Group | Edema | Inflammation | Hemorrhage | Area of necrosis | Total damage |
|---|---|---|---|---|---|
| Normal control | 0.00 ± 0.00 | 0.17 ± 0.28 | 0.00 ± 0.00 | 0.00 ± 0.00 | 0.17 ± 0.28 |
| Sham control | 0.22 ± 0.27 | 0.56 ± 0.72 | 0.06 ± 0.14 | 0.17 ± 0.41 | 1.00 ± 1.33 |
| Model control | 2.22 ± 0.65 | 3.56 ± 0.53 | 2.41 ± 0.76 | 2.11 ± 0.44 | 10.30 ± 1.87 |
| Peptide 12-L | 1.33 ± 0.86 | 2.90 ± 1.22 | 1.73 ± 0.89 | 1.63 ± 0.74 | 7.60 ± 3.07 |
| Peptide 12-M | 1.44 ± 0.87 | 2.83 ± 0.93 | 1.31 ± 0.87 | 1.11 ± 0.78 | 6.69 ± 2.53 |
| Peptide 12-H | 1.21 ± 0.96 | 2.67 ± 1.00 | 1.15 ± 0.83 | 1.13 ± 0.85 | 6.15 ± 2.69 |

As it indicated in FIG. 4 to FIG. 8, one can clearly see that administration of peptide 12 can reduce the pathological changes of pancreas caused by sodium taurocholate in a dose-dependent manner.

Example 2. Effects of Peptide 12 on Caerulein Induced Pancreatitis Model

Male BALB/c mice, aged 6-8 weeks, were accumulated for more than 7 days. After fasting overnight, 10 animals were randomly selected as normal control. The remaining animals were injected with caerulein 50 μg/kg intraperitoneally every 1 hour for 10 times to induce acute pancreatitis, and they were randomly divided into model control group and peptide 12 treatment groups with the dosage of 0.025, 0.25, 2.5 and 25 mg/kg respectively, there were 10 mice in each group. Mice were given corresponding doses of peptide 12 or normal saline 5 minutes before the fourth injection of caerulein.

The experiment was finished one hour after the 10th injection of caerulein, blood samples were collected for the determination of amylase and lipase levels. Pancreas were weighed and fixed in 10% formalin solution for subsequent pathological analysis.

The pancreatic index was calculated as pancreatic weight/ body weight, which reflected the severity of pancreatic edema. The statistical results were shown in FIG. 9, in which ### means $P<0.001$ compared with the normal control group;  means $P<0.01$ compared with the model control group, * means $P<0.001$ compared with the model control group. As showed in FIG. 9, the pancreatic index was significantly increased in the model group comparing to the normal control group, pancreatic indexes were significantly decreased at the doses of 0.025, 0.25 and 2.5 mg/kg of peptide 12 treatment groups in a dose dependent manner. As shown in FIG. 10 and FIG. 11, the levels of amylase and lipase were significantly increased in the model control group compared with those in the normal control group. Compared with the model control group, the levels of the amylase and lipase in the Peptide 12 at the doses of 0.025, 0.25, 2.5 and 25 mg/kg treatment groups were significantly lowered. It should be noted that in FIG. 10, ### means $P<0.001$ compared with the normal control group; * means $P<0.001$ compared with the model control group; in FIG. 11, ### means $P<0.001$ compared with the normal control group; * means $P<0.001$ compared with the model control group.

The severity of pancreatic injury was assessed by preparing HE slices of pancreas and using Schmidt's scoring standard to evaluate the pathological changes of pancreatic edema, inflammation, hemorrhage and necrosis.

TABLE 8

Pathological scores of each group

| Group | Edema | Inflammation | Hemorrhage | Area of necrosis |
|---|---|---|---|---|
| Normal control | 0.00 ± 0.00 | 0.00 ± 0.00 | 0.00 ± 0.00 | 0.00 ± 0.00 |
| Model control | 2.00 ± 0.89 | 2.33 ± 0.82 | 0.00 ± 0.00 | 0.00 ± 0.00 |
| Peptide 12-0.025 | 1.50 ± 0.84 | 1.33 ± 0.52 | 0.00 ± 0.00 | 0.00 ± 0.00 |
| Peptide 12-0.25 | 1.67 ± 0.82 | 1.17 ± 0.75 | 0.00 ± 0.00 | 0.00 ± 0.00 |
| Peptide 12-2.5 | 1.17 ± 1.17 | 0.83 ± 0.75 | 0.00 ± 0.00 | 0.00 ± 0.00 |
| Peptide 12-25 | 1.50 ± 0.55 | 2.17 ± 0.75 | 0.33 ± 0.82 | 0.00 ± 0.00 |

The pathological scoring results showed that there was no obvious hemorrhage and necrosis in the model of caerulein-induced pancreatitis, and the scoring results of edema and inflammation were shown in FIG. 12 and FIG. 13. It should be noted that in FIG. 12, ### means $P<0.001$ compared with the normal control group; in FIG. 13, ### means $P<0.001$ compared with the normal control group, * means $P<0.05$, ** means $P<0.01$ compared with the model control group. From FIG. 12 to FIG. 13, it can be seen that the model group has obvious edema and inflammation damage compared with the normal control group, and the edema and inflammation of the pancreas were all alleviated with the treatment of peptide 12.

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

The invention claimed is:

1. A method for treating acute pancreatitis comprising administering to a patient having acute pancreatitis a pharmaceutical composition comprising an INGAP-PP peptide selected from:

| TABLE 2 | |
|---|---|
| 1 | H-IGLHDPSHGTLPNGS-OH |
| 6 | H-IGLHAPSHGTLPNGS-OH |
| 7 | H-IGLHDPSHGTLPAGS-OH |
| 8 | H-IGLHAPSHGTLPAGS-OH |
| 9 | H-IGLHDPSHGTLPAGSK-OH |
| 10 | H-IGLHDPSHGTLP(Aib)GS-OH |
| 11 | H-IGLHDPSHGTLP(N-methyl-L-Alanine)GS-OH |
| 12 | Ac-IGLHDPSHGTLPAGS-OH |
| 13 | H-(D-Isoleucine)GLHDPSHGTLPAGS-OH |
| 14 | H-(L-NorValine)GLHDPSHGTLPAGS-OH |
| 15 | H-(L-NorLeucine)GLHDPSHGTLPAGS-OH |
| 16 | Ac-IGLHDPSHGTLPNGS-OH |
| 17 | H-(D-Isoleucine)GLHDPSHGTLPNGS-OH |
| 18 | H-IGLHDPSHGTEPNGS-OH |
| 19 | H-IGLHDPSQGTLPNGS-OH |
| 20 | H-IGLHDPTHGTLPNGS-OH |
| 21 | H-IGLHDPSHGTLPNGE-OH |
| 22 | H-IGLHDPSHGTLPNGK-OH |
| 23 | H-IGLHDPSHGTLPAGK-OH |
| 24 | H-IGLHDPSHGTEPAGS-OH |
| 25 | H-IGLHDPSQGTLPAGS-OH |
| 26 | H-IGLHDPTHGTLPAGS-OH |
| 27 | H-IGLHDPSHGTLPAGE-OH |
| 28 | H-IGLHDPSHGTLPAG-NH2 |
| 29 | Ac-IGLHDPSHGTLPAGS-NH2 |

| TABLE 2-continued | |
|---|---|
| 30 | Ac-IGLHDPSHGTLPAG-NH2 |
| 31 | Ac-IGLHDPSHGTLPNGS-NH2 |
| 32 | H-IGLHDPSHGTLPNGS-NH2 |
| 33 | H-IGLHDPSHGTLPNGSC-OH |
| 34 | Ac-IGLHDPSHGTLPNGSC-OH |
| 35 | H-IGLHDPSHGTLPNGSC-NH2 |
| 36 | Ac-IGLHDPSHGTLPNGSC-NH2 |
| 37 | H-IGLHDPSHGTLPNGC-OH |
| 38 | Ac-IGLHDPSHGTLPNGC-OH |
| 39 | H-IGLHDPSHGTLPNGC-NH2 |
| 40 | Ac-IGLHDPSHGTLPNGC-NH2 |
| 41 | H-IGLHDPSHGTLPAGS-NH2 |
| 42 | H-IGLHDPSHGTLPAGSC-OH |
| 43 | Ac-IGLHDPSHGTLPAGSC-OH |
| 44 | H-IGLHDPSHGTLPAGSC-NH2 |
| 45 | Ac-IGLHDPSHGTLPAGSC-NH2 |
| 46 | H-IGLHDPSHGTLPAGC-OH |
| 47 | Ac-IGLHDPSHGTLPAGC-OH |
| 48 | H-IGLHDPSHGTLPAGC-NH2 |
| 49 | Ac-IGLHDPSHGTLPAGC-NH2 |
| 73 | IGLHDPSHGTLPAG |
| 74 | IGLHDPSHGTLPNG |
| 75 | Ac-IGLHDPSHGTLPNG |
| 76 | IGLHDPSHGTLPNG-NH2 |
| 77 | Ac-IGLHDPSHGTLPNG-NH2 |
| 78 | H-IGLHDPSHGTLPQGS-OH |
| 79 | H-IGLHDPSHGTLPDGS-OH |
| 80 | H-IGLHDPSHGTLPEGS-OH |

TABLE 2-continued

| | |
|---|---|
| 81 | H-IGLHEPSHGTLPNGS-OH |
| 82 | H-IGLHQPSHGTLPNGS-OH |
| 83 | H-IGLHNPSHGTLPNGS-OH |
| 84 | H-IGLHEPSHGTLPAGS-OH |
| 85 | H-IGLHQPSHGTLPAGS-OH |
| 86 | H-IGLHNPSHGTLPAGS-OH |
| 87 | H-IGLHDPSHGTLPQGSC-OH |
| 88 | H-IGLHDPSHGTLPDGSC-OH |
| 89 | H-IGLHDPSHGTLPEGSC-OH |
| 90 | H-IGLHEPSHGTLPNGSC-OH |
| 91 | H-IGLHQPSHGTLPNGSC-OH |
| 92 | H-IGLHNPSHGTLPNGSC-OH |
| 93 | H-IGLHDPSHGTLPQG-OH |
| 94 | H-IGLHDPSHGTLPDG-OH |
| 95 | H-IGLHDPSHGTLPEG-OH |
| 96 | H-IGLHEPSHGTLPNG-OH |
| 97 | H-IGLHQPSHGTLPNG-OH |
| 98 | H-IGLHNPSHGTLPNG-OH |
| 99 | H-IGLHEPSHGTLPAG-OH |
| 100 | H-IGLHQPSHGTLPAG-OH |
| 101 | H-IGLHNPSHGTLPAG-OH |
| 102 | H-IGLHDPSHGTLPQGE-OH |
| 103 | H-IGLHDPSHGTLPDGE-OH |
| 104 | H-IGLHDPSHGTLPEGE-OH |
| 105 | H-IGLHEPSHGTLPNGE-OH |
| 106 | H-IGLHQPSHGTLPNGE-OH |
| 107 | H-IGLHNPSHGTLPNGE-OH |
| 108 | H-IGLHEPSHGTLPAGE-OH |
| 109 | H-IGLHQPSHGTLPAGE-OH |
| 110 | H-IGLHNPSHGTLPAGE-OH. |

2. The method of claim 1, wherein the INGAP-PP peptide is SEQ ID NO: 12.

3. The method of claim 2, wherein the INGAP-PP peptide is administered at a dose of about 0.025 mg/Kg to about 2.5 mg/Kg per day.

4. A method for treating acute pancreatitis by lowering the levels of amylase and lipase in the blood of a patient having acute pancreatitis comprising administering the patient a pharmaceutical composition comprising an INGAP-PP peptide selected from:

TABLE 2

| | |
|---|---|
| 1 | H-IGLHDPSHGTLPNGS-OH |
| 6 | H-IGLHAPSHGTLPNGS-OH |

TABLE 2-continued

| | |
|---|---|
| 7 | H-IGLHDPSHGTLPAGS-OH |
| 8 | H-IGLHAPSHGTLPAGS-OH |
| 9 | H-IGLHDPSHGTLPAGSK-OH |
| 10 | H-IGLHDPSHGTLP(Aib)GS-OH |
| 11 | H-IGLHDPSHGTLP(N-methyl-L-Alanine)GS-OH |
| 12 | Ac-IGLHDPSHGTLPAGS-OH |
| 13 | H-(D-Isoleucine)GLHDPSHGTLPAGS-OH |
| 14 | H-(L-NorValine)GLHDPSHGTLPAGS-OH |
| 15 | H-(L-NorLeucine)GLHDPSHGTLPAGS-OH |
| 16 | Ac-IGLHDPSHGTLPNGS-OH |
| 17 | H-(D-Isoleucine)GLHDPSHGTLPNGS-OH |
| 18 | H-IGLHDPSHGTEPNGS-OH |
| 19 | H-IGLHDPSQGTLPNGS-OH |
| 20 | H-IGLHDPTHGTLPNGS-OH |
| 21 | H-IGLHDPSHGTLPNGE-OH |
| 22 | H-IGLHDPSHGTLPNGK-OH |
| 23 | H-IGLHDPSHGTLPAGK-OH |
| 24 | H-IGLHDPSHGTEPAGS-OH |
| 25 | H-IGLHDPSQGTLPAGS-OH |
| 26 | H-IGLHDPTHGTLPAGS-OH |
| 27 | H-IGLHDPSHGTLPAGE-OH |
| 28 | H-IGLHDPSHGTLPAG-NH2 |
| 29 | Ac-IGLHDPSHGTLPAGS-NH2 |
| 30 | Ac-IGLHDPSHGTLPAG-NH2 |
| 31 | Ac-IGLHDPSHGTLPNGS-NH2 |
| 32 | H-IGLHDPSHGTLPNGS-NH2 |
| 33 | H-IGLHDPSHGTLPNGSC-OH |
| 34 | Ac-IGLHDPSHGTLPNGSC-OH |
| 35 | H-IGLHDPSHGTLPNGSC-NH2 |
| 36 | Ac-IGLHDPSHGTLPNGSC-NH2 |
| 37 | H-IGLHDPSHGTLPNGC-OH |
| 38 | Ac-IGLHDPSHGTLPNGC-OH |
| 39 | H-IGLHDPSHGTLPNGC-NH2 |
| 40 | Ac-IGLHDPSHGTLPNGC-NH2 |
| 41 | H-IGLHDPSHGTLPAGS-NH2 |
| 42 | H-IGLHDPSHGTLPAGSC-OH |
| 43 | Ac-IGLHDPSHGTLPAGSC-OH |
| 44 | H-IGLHDPSHGTLPAGSC-NH2 |
| 45 | Ac-IGLHDPSHGTLPAGSC-NH2 |

TABLE 2-continued

| | |
|---|---|
| 46 | H-IGLHDPSHGTLPAGC-OH |
| 47 | Ac-IGLHDPSHGTLPAGC-OH |
| 48 | H-IGLHDPSHGTLPAGC-NH2 |
| 49 | Ac-IGLHDPSHGTLPAGC-NH2 |
| 73 | IGLHDPSHGTLPAG |
| 74 | IGLHDPSHGTLPNG |
| 75 | Ac-IGLHDPSHGTLPNG |
| 76 | IGLHDPSHGTLPNG-NH2 |
| 77 | Ac-IGLHDPSHGTLPNG-NH2 |
| 78 | H-IGLHDPSHGTLPQGS-OH |
| 79 | H-IGLHDPSHGTLPDGS-OH |
| 80 | H-IGLHDPSHGTLPEGS-OH |
| 81 | H-IGLHEPSHGTLPNGS-OH |
| 82 | H-IGLHQPSHGTLPNGS-OH |
| 83 | H-IGLHNPSHGTLPNGS-OH |
| 84 | H-IGLHEPSHGTLPAGS-OH |
| 85 | H-IGLHQPSHGTLPAGS-OH |
| 86 | H-IGLHNPSHGTLPAGS-OH |
| 87 | H-IGLHDPSHGTLPQGSC-OH |
| 88 | H-IGLHDPSHGTLPDGSC-OH |
| 89 | H-IGLHDPSHGTLPEGSC-OH |
| 90 | H-IGLHEPSHGTLPNGSC-OH |
| 91 | H-IGLHQPSHGTLPNGSC-OH |

TABLE 2-continued

| | |
|---|---|
| 92 | H-IGLHNPSHGTLPNGSC-OH |
| 93 | H-IGLHDPSHGTLPQG-OH |
| 94 | H-IGLHDPSHGTLPDG-OH |
| 95 | H-IGLHDPSHGTLPEG-OH |
| 96 | H-IGLHEPSHGTLPNG-OH |
| 97 | H-IGLHQPSHGTLPNG-OH |
| 98 | H-IGLHNPSHGTLPNG-OH |
| 99 | H-IGLHEPSHGTLPAG-OH |
| 100 | H-IGLHQPSHGTLPAG-OH |
| 101 | H-IGLHNPSHGTLPAG-OH |
| 102 | H-IGLHDPSHGTLPQGE-OH |
| 103 | H-IGLHDPSHGTLPDGE-OH |
| 104 | H-IGLHDPSHGTLPEGE-OH |
| 105 | H-IGLHEPSHGTLPNGE-OH |
| 106 | H-IGLHQPSHGTLPNGE-OH |
| 107 | H-IGLHNPSHGTLPNGE-OH |
| 108 | H-IGLHEPSHGTLPAGE-OH |
| 109 | H-IGLHQPSHGTLPAGE-OH |
| 110 | H-IGLHNPSHGTLPAGE-OH. |

5. The method of claim 3, wherein the INGAP-PP peptide is SEQ ID NO: 12.

6. The method of claim 5, wherein the INGAP-PP peptide is administered at a dose of about 0.025 mg/Kg to about 2.5 mg/Kg per day.

* * * * *

SEQUENCE LISTING

```
<160> NUMBER OF SEQ ID NOS: 117

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Gly Leu His Asp Pro Ser His Gly Thr Leu Pro Asn Gly Ser
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Gly Leu His Asp Pro Thr Gln Gly Thr Glu Pro Asn Gly Glu
1               5                   10                  15

<210> SEQ ID NO 3

<400> SEQUENCE: 3

000
```

```
<210> SEQ ID NO 4
<400> SEQUENCE: 4

000

<210> SEQ ID NO 5
<400> SEQUENCE: 5

000

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Gly Leu His Ala Pro Ser His Gly Thr Leu Pro Asn Gly Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Gly Leu His Asp Pro Ser His Gly Thr Leu Pro Ala Gly Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Gly Leu His Ala Pro Ser His Gly Thr Leu Pro Ala Gly Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Gly Leu His Asp Pro Ser His Gly Thr Leu Pro Ala Gly Ser Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (13)..(13)
<223> OTHER INFORMATION: Aib

<400> SEQUENCE: 10

Ile Gly Leu His Asp Pro Ser His Gly Thr Leu Pro Xaa Gly Ser
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: N-methyl-L-Ala

<400> SEQUENCE: 11

Ile Gly Leu His Asp Pro Ser His Gly Thr Leu Pro Ala Gly Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Gly Leu His Asp Pro Ser His Gly Thr Leu Pro Ala Gly Ser
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ile

<400> SEQUENCE: 13

Ile Gly Leu His Asp Pro Ser His Gly Thr Leu Pro Ala Gly Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nva

<400> SEQUENCE: 14

Val Gly Leu His Asp Pro Ser His Gly Thr Leu Pro Ala Gly Ser
1               5                   10                  15

<210> SEQ ID NO 15
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle

<400> SEQUENCE: 15

Leu Gly Leu His Asp Pro Ser His Gly Thr Leu Pro Ala Gly Ser
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Gly Leu His Asp Pro Ser His Gly Thr Leu Pro Asn Gly Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ile

<400> SEQUENCE: 17

Ile Gly Leu His Asp Pro Ser His Gly Thr Leu Pro Asn Gly Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Gly Leu His Asp Pro Ser His Gly Thr Glu Pro Asn Gly Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Gly Leu His Asp Pro Ser Gln Gly Thr Leu Pro Asn Gly Ser
1               5                   10                  15

<210> SEQ ID NO 20
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 20

Ile Gly Leu His Asp Pro Thr His Gly Thr Leu Pro Asn Gly Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Gly Leu His Asp Pro Ser His Gly Thr Leu Pro Asn Gly Glu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Gly Leu His Asp Pro Ser His Gly Thr Leu Pro Asn Gly Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Gly Leu His Asp Pro Ser His Gly Thr Leu Pro Ala Gly Lys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Gly Leu His Asp Pro Ser His Gly Thr Glu Pro Ala Gly Ser
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Gly Leu His Asp Pro Ser Gln Gly Thr Leu Pro Ala Gly Ser
1               5                   10                  15
```

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Gly Leu His Asp Pro Thr His Gly Thr Leu Pro Ala Gly Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Gly Leu His Asp Pro Ser His Gly Thr Leu Pro Ala Gly Glu
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Gly Leu His Asp Pro Ser His Gly Thr Leu Pro Ala Gly
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Gly Leu His Asp Pro Ser His Gly Thr Leu Pro Ala Gly Ser
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Gly Leu His Asp Pro Ser His Gly Thr Leu Pro Ala Gly
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Gly Leu His Asp Pro Ser His Gly Thr Leu Pro Asn Gly Ser
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Gly Leu His Asp Pro Ser His Gly Thr Leu Pro Asn Gly Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Gly Leu His Asp Pro Ser His Gly Thr Leu Pro Asn Gly Ser Cys
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Gly Leu His Asp Pro Ser His Gly Thr Leu Pro Asn Gly Ser Cys
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Gly Leu His Asp Pro Ser His Gly Thr Leu Pro Asn Gly Ser Cys
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Gly Leu His Asp Pro Ser His Gly Thr Leu Pro Asn Gly Ser Cys
1               5                   10                  15

<210> SEQ ID NO 37
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Gly Leu His Asp Pro Ser His Gly Thr Leu Pro Asn Gly Cys
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Gly Leu His Asp Pro Ser His Gly Thr Leu Pro Asn Gly Cys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Gly Leu His Asp Pro Ser His Gly Thr Leu Pro Asn Gly Cys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Gly Leu His Asp Pro Ser His Gly Thr Leu Pro Asn Gly Cys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Gly Leu His Asp Pro Ser His Gly Thr Leu Pro Ala Gly Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Gly Leu His Asp Pro Ser His Gly Thr Leu Pro Ala Gly Ser Cys
```

```
1               5                   10                  15
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Ile Gly Leu His Asp Pro Ser His Gly Thr Leu Pro Ala Gly Ser Cys
1               5                   10                  15
```

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Ile Gly Leu His Asp Pro Ser His Gly Thr Leu Pro Ala Gly Ser Cys
1               5                   10                  15
```

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Ile Gly Leu His Asp Pro Ser His Gly Thr Leu Pro Ala Gly Ser Cys
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ile Gly Leu His Asp Pro Ser His Gly Thr Leu Pro Ala Gly Cys
1               5                   10                  15
```

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Ile Gly Leu His Asp Pro Ser His Gly Thr Leu Pro Ala Gly Cys
1               5                   10                  15
```

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Ile Gly Leu His Asp Pro Ser His Gly Thr Leu Pro Ala Gly Cys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Gly Leu His Asp Pro Ser His Gly Thr Leu Pro Ala Gly Cys
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Gly Leu His Asp Pro Thr Gln Gly Thr Glu Pro Ala Gly Glu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aib

<400> SEQUENCE: 51

Ile Gly Leu His Asp Pro Thr Gln Gly Thr Glu Pro Xaa Gly Glu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Gly Leu His Asp Pro Thr Gln Gly Thr Glu Pro Ala Gly Glu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ile

```
<400> SEQUENCE: 53

Ile Gly Leu His Asp Pro Thr Gln Gly Thr Glu Pro Ala Gly Glu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Gly Leu His Asp Pro Thr Gln Gly Thr Glu Pro Asn Gly Glu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ile

<400> SEQUENCE: 55

Ile Gly Leu His Asp Pro Thr Gln Gly Thr Glu Pro Asn Gly Glu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Gly Leu His Asp Pro Thr Gln Gly Thr Glu Pro Asn Gly Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Gly Leu His Asp Pro Thr Gln Gly Thr Glu Pro Ala Gly Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Gly Leu His Asp Pro Thr Gln Gly Thr Leu Pro Asn Gly Glu
1               5                   10                  15
```

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Gly Leu His Asp Pro Thr Gln Gly Thr Leu Pro Ala Gly Glu
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Gly Leu His Asp Pro Thr Gln Gly Thr Glu Pro Ala Gly
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Gly Leu His Asp Pro Thr Gln Gly Thr Glu Pro Asn Gly Glu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Gly Leu His Asp Pro Thr Gln Gly Thr Glu Pro Ala Gly Glu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Gly Leu His Asp Pro Thr Gln Gly Thr Glu Pro Asn Gly Glu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Gly Leu His Asp Pro Thr Gln Gly Thr Glu Pro Asn Gly Cys
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Gly Leu His Asp Pro Thr Gln Gly Thr Glu Pro Asn Gly Cys
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Gly Leu His Asp Pro Thr Gln Gly Thr Glu Pro Asn Gly Cys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Gly Leu His Asp Pro Thr Gln Gly Thr Glu Pro Asn Gly Cys
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Gly Leu His Asp Pro Thr Gln Gly Thr Glu Pro Ala Gly Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Gly Leu His Asp Pro Thr Gln Gly Thr Glu Pro Ala Gly Cys
1               5                   10                  15

<210> SEQ ID NO 70
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Gly Leu His Asp Pro Thr Gln Gly Thr Glu Pro Ala Gly Cys
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Gly Leu His Asp Pro Thr Gln Gly Thr Glu Pro Ala Gly Cys
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Gly Leu His Asp Pro Thr Gln Gly Thr Glu Pro Ala Gly Cys
1               5                   10                  15

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Gly Leu His Asp Pro Ser His Gly Thr Leu Pro Ala Gly
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Gly Leu His Asp Pro Ser His Gly Thr Leu Pro Asn Gly
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Gly Leu His Asp Pro Ser His Gly Thr Leu Pro Asn Gly
```

```
1               5                   10
```

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Ile Gly Leu His Asp Pro Ser His Gly Thr Leu Pro Asn Gly
1               5                   10
```

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Ile Gly Leu His Asp Pro Ser His Gly Thr Leu Pro Asn Gly
1               5                   10
```

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Ile Gly Leu His Asp Pro Ser His Gly Thr Leu Pro Gln Gly Ser
1               5                   10                  15
```

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Ile Gly Leu His Asp Pro Ser His Gly Thr Leu Pro Asp Gly Ser
1               5                   10                  15
```

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Ile Gly Leu His Asp Pro Ser His Gly Thr Leu Pro Glu Gly Ser
1               5                   10                  15
```

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Ile Gly Leu His Glu Pro Ser His Gly Thr Leu Pro Asn Gly Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Gly Leu His Gln Pro Ser His Gly Thr Leu Pro Asn Gly Ser
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Gly Leu His Asn Pro Ser His Gly Thr Leu Pro Asn Gly Ser
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Gly Leu His Glu Pro Ser His Gly Thr Leu Pro Ala Gly Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ile Gly Leu His Gln Pro Ser His Gly Thr Leu Pro Ala Gly Ser
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Gly Leu His Asn Pro Ser His Gly Thr Leu Pro Ala Gly Ser
1               5                   10                  15

<210> SEQ ID NO 87

-continued

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ile Gly Leu His Asp Pro Ser His Gly Thr Leu Pro Gln Gly Ser Cys
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ile Gly Leu His Asp Pro Ser His Gly Thr Leu Pro Asp Gly Ser Cys
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Gly Leu His Asp Pro Ser His Gly Thr Leu Pro Glu Gly Ser Cys
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Gly Leu His Glu Pro Ser His Gly Thr Leu Pro Asn Gly Ser Cys
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ile Gly Leu His Gln Pro Ser His Gly Thr Leu Pro Asn Gly Ser Cys
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92
```

Ile Gly Leu His Asn Pro Ser His Gly Thr Leu Pro Asn Gly Ser Cys
1               5                   10                  15

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Gly Leu His Asp Pro Ser His Gly Thr Leu Pro Gln Gly
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Gly Leu His Asp Pro Ser His Gly Thr Leu Pro Asp Gly
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Gly Leu His Asp Pro Ser His Gly Thr Leu Pro Glu Gly
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ile Gly Leu His Glu Pro Ser His Gly Thr Leu Pro Asn Gly
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Gly Leu His Gln Pro Ser His Gly Thr Leu Pro Asn Gly
1               5                   10

<210> SEQ ID NO 98
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 98

Ile Gly Leu His Asn Pro Ser His Gly Thr Leu Pro Asn Gly
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Gly Leu His Glu Pro Ser His Gly Thr Leu Pro Ala Gly
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Gly Leu His Gln Pro Ser His Gly Thr Leu Pro Ala Gly
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ile Gly Leu His Asn Pro Ser His Gly Thr Leu Pro Ala Gly
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Gly Leu His Asp Pro Ser His Gly Thr Leu Pro Gln Gly Glu
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Gly Leu His Asp Pro Ser His Gly Thr Leu Pro Asp Gly Glu
1               5                   10                  15

```
<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Gly Leu His Asp Pro Ser His Gly Thr Leu Pro Glu Gly Glu
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Gly Leu His Glu Pro Ser His Gly Thr Leu Pro Asn Gly Glu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ile Gly Leu His Gln Pro Ser His Gly Thr Leu Pro Asn Gly Glu
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Gly Leu His Asn Pro Ser His Gly Thr Leu Pro Asn Gly Glu
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Gly Leu His Glu Pro Ser His Gly Thr Leu Pro Ala Gly Glu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109
```

```
Ile Gly Leu His Gln Pro Ser His Gly Thr Leu Pro Ala Gly Glu
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ile Gly Leu His Asn Pro Ser His Gly Thr Leu Pro Ala Gly Glu
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, D-Ile, Nva or Nle
<220> FEATURE:
<221> NAME/KEY: MOD_RES
<222> LOCATION: (5)..(5)
<223> OTHER INFORMATION: Ala or Asp
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: His or Gln
<220> FEATURE:
<221> NAME/KEY: MOD_RES
<222> LOCATION: (11)..(11)
<223> OTHER INFORMATION: Leu or Glu
<220> FEATURE:
<221> NAME/KEY: MOD_RES
<222> LOCATION: (13)..(13)
<223> OTHER INFORMATION: Ala, Asn, Aib or N-Methyl-L-Ala

<400> SEQUENCE: 111

Xaa Gly Leu His Xaa Pro Xaa Xaa Gly Thr Xaa Pro Xaa Gly Ser
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Glu, Cys or Lys
<220> FEATURE:
<221> NAME/KEY: MISC_FEATURE
<222> LOCATION: (16)..(16)
<223> OTHER INFORMATION: May or may not be present

<400> SEQUENCE: 112

Ile Gly Leu His Asp Pro Ser His Gly Thr Leu Pro Asn Gly Xaa Cys
1               5                   10                  15
```

```
<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Glu, Cys, Lys or not present

<400> SEQUENCE: 113

Ile Gly Leu His Asp Pro Ser His Gly Thr Leu Pro Ala Gly Xaa
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Lys or Cys

<400> SEQUENCE: 114

Ile Gly Leu His Asp Pro Ser His Gly Thr Leu Pro Ala Gly Ser Xaa
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or D-Ile
<220> FEATURE:
<221> NAME/KEY: MOD_RES
<222> LOCATION: (11)..(11)
<223> OTHER INFORMATION: Glu or Leu
<220> FEATURE:
<221> NAME/KEY: MOD_RES
<222> LOCATION: (13)..(13)
<223> OTHER INFORMATION: Ala, Asn or Aib

<400> SEQUENCE: 115

Xaa Gly Leu His Asp Pro Thr Gln Gly Thr Xaa Pro Xaa Gly Glu
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Glu or Cys

<400> SEQUENCE: 116

Ile Gly Leu His Asp Pro Thr Gln Gly Thr Glu Pro Asn Gly Xaa
1               5                   10                  15
```

```
<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Cys or not present

<400> SEQUENCE: 117

Ile Gly Leu His Asp Pro Thr Gln Gly Thr Glu Pro Ala Gly Xaa
1               5                   10                  15
```